(12) United States Patent
Angibaud

(10) Patent No.: US 9,393,124 B2
(45) Date of Patent: Jul. 19, 2016

(54) PATELLA IMPLANT SYSTEMS AND PATELLA TRIALS FOR SELECTING SAME

(71) Applicant: Exactech, Inc., Gainesville, FL (US)

(72) Inventor: Laurent Angibaud, Gainesville, FL (US)

(73) Assignee: Exactech, Inc., Gainesville, FL (US)

( * ) Notice: Subject to any disclaimer, the term of this patent is extended or adjusted under 35 U.S.C. 154(b) by 115 days.

(21) Appl. No.: 14/092,423

(22) Filed: Nov. 27, 2013

(65) Prior Publication Data

US 2014/0148909 A1    May 29, 2014

Related U.S. Application Data

(60) Provisional application No. 61/731,150, filed on Nov. 29, 2012.

(51) Int. Cl.
*A61F 2/38* (2006.01)
*A61F 2/46* (2006.01)
*A61F 2/30* (2006.01)

(52) U.S. Cl.
CPC ............ *A61F 2/3877* (2013.01); *A61F 2/4684* (2013.01); *A61F 2002/3038* (2013.01); *A61F 2002/30125* (2013.01); *A61F 2002/30553* (2013.01); *A61F 2002/30878* (2013.01)

(58) Field of Classification Search
CPC ............... A61F 2/3877; A61F 2/4684; A61F 2002/30604; A61B 17/158
See application file for complete search history.

(56) References Cited

U.S. PATENT DOCUMENTS

| | | | |
|---|---|---|---|
| 5,609,644 A * | 3/1997 | Ashby | 623/20.2 |
| 6,589,248 B1 * | 7/2003 | Hughes | 606/102 |
| 8,556,982 B2 | 10/2013 | Wright et al. | |
| 2007/0150066 A1 * | 6/2007 | McMinn | 623/20.19 |
| 2012/0179264 A1 | 7/2012 | Todd et al. | |

* cited by examiner

*Primary Examiner* — Brian Dukert
(74) *Attorney, Agent, or Firm* — Greenberg Traurig, LLP

(57) ABSTRACT

A system includes a patella trial comprising a baseplate and an articular surface member configured to move along at least one of a medial-lateral axis or a superior-inferior axis of the baseplate; and an implant comprising a posterior articular surface and an anterior surface, wherein the anterior surface has a medial/lateral width with a midpoint, wherein the posterior articular surface has a posterior-most point, wherein an imaginary line extending through the posterior-most point is parallel to an imaginary line extending through the midpoint, and wherein a distance (I) is defined by measuring a length between the imaginary line extending through the posterior-most point and the imaginary line extending through the midpoint; wherein the implant is selected from a set of implants each having a different I, and wherein the chosen implant is selected based on an offset of the articular surface member relative to the baseplate on the patella trial.

19 Claims, 22 Drawing Sheets

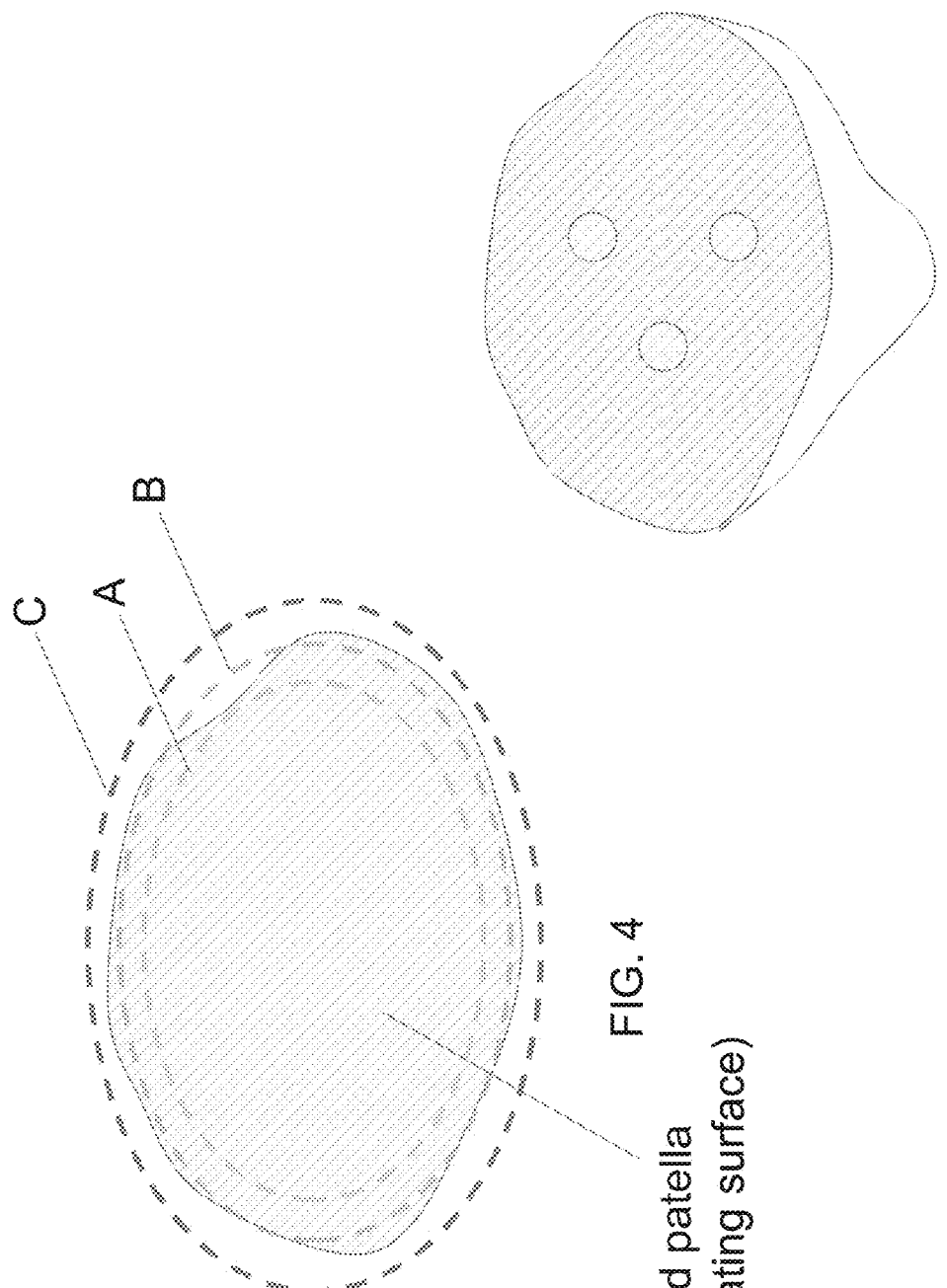

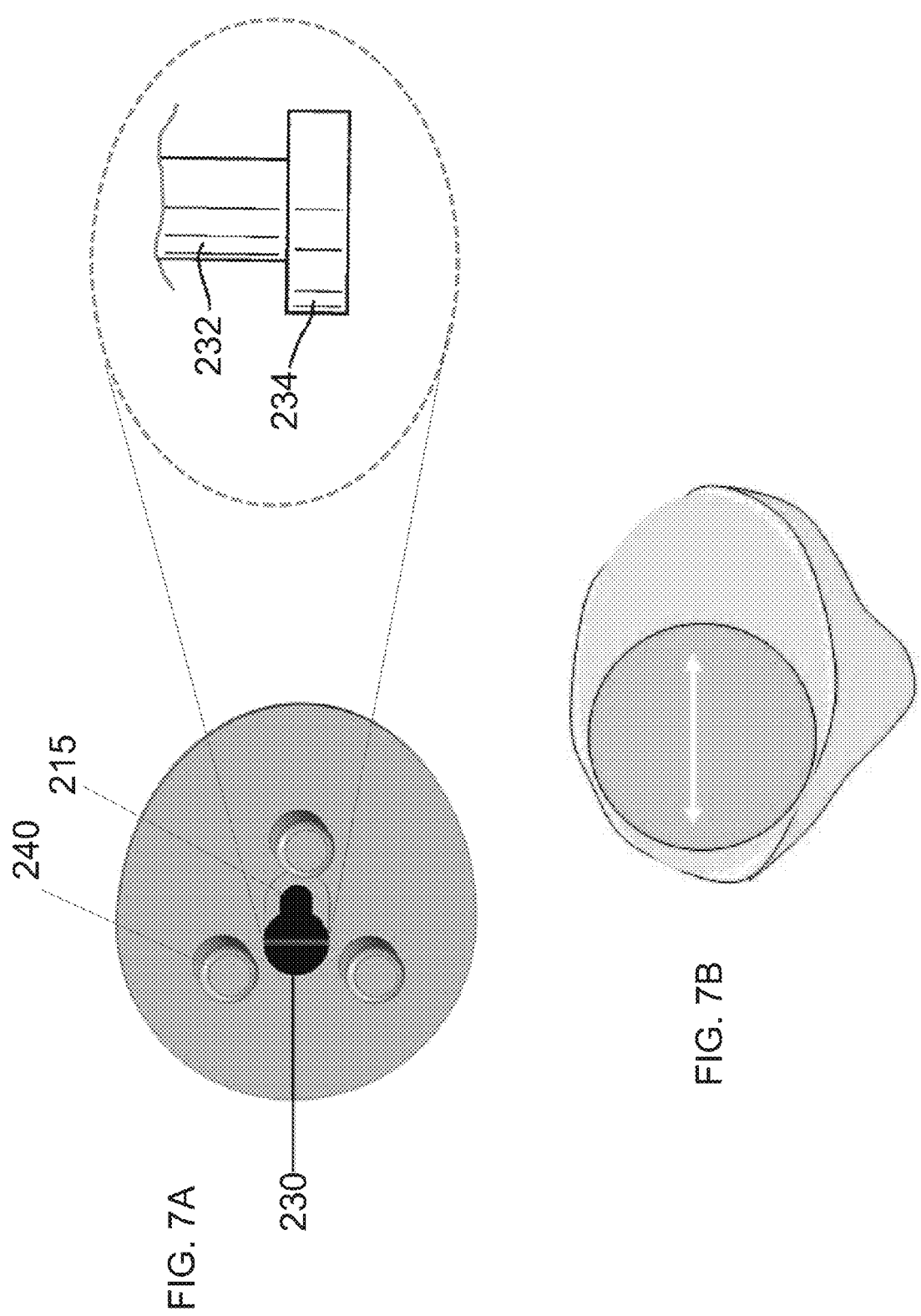

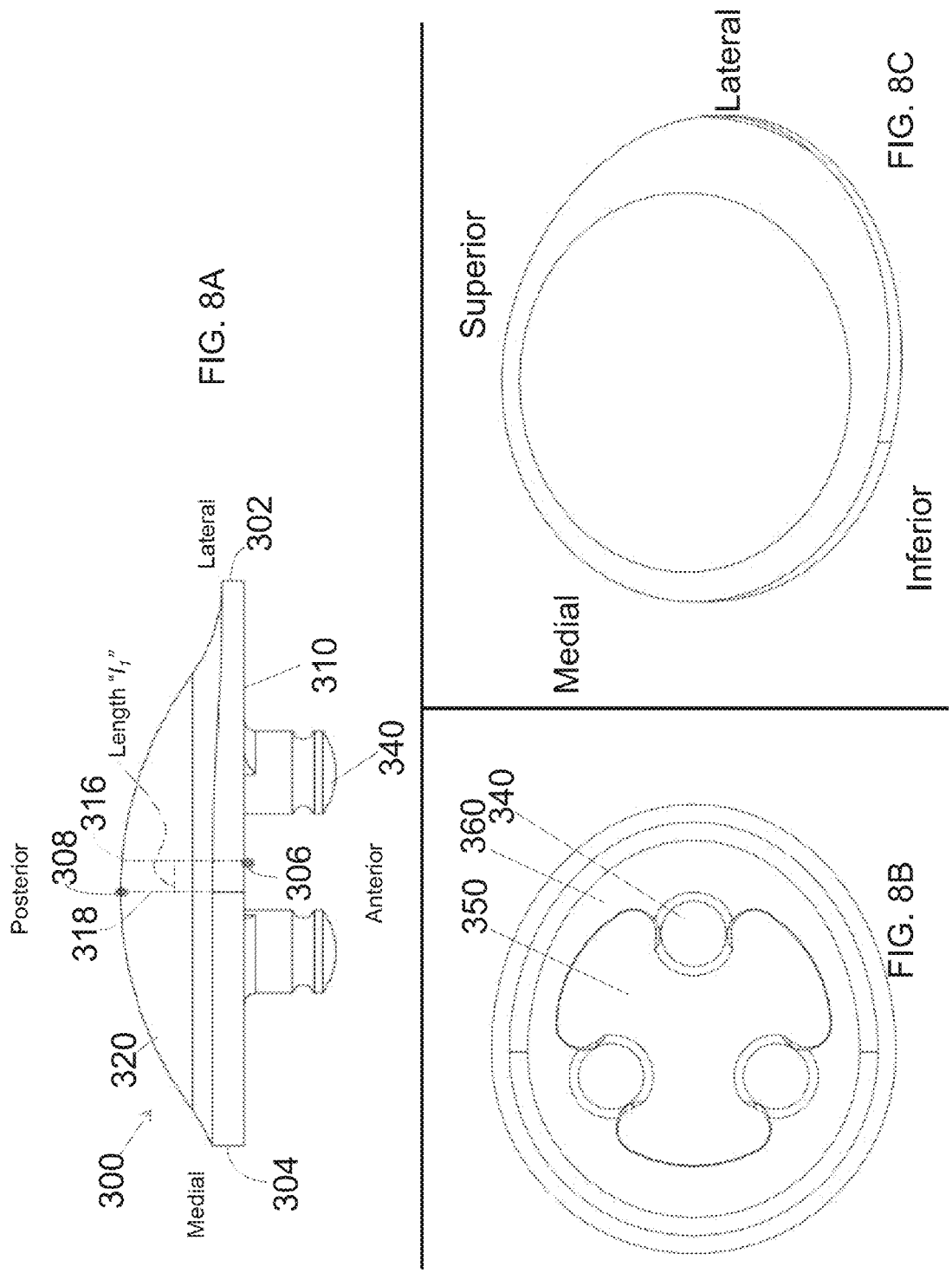

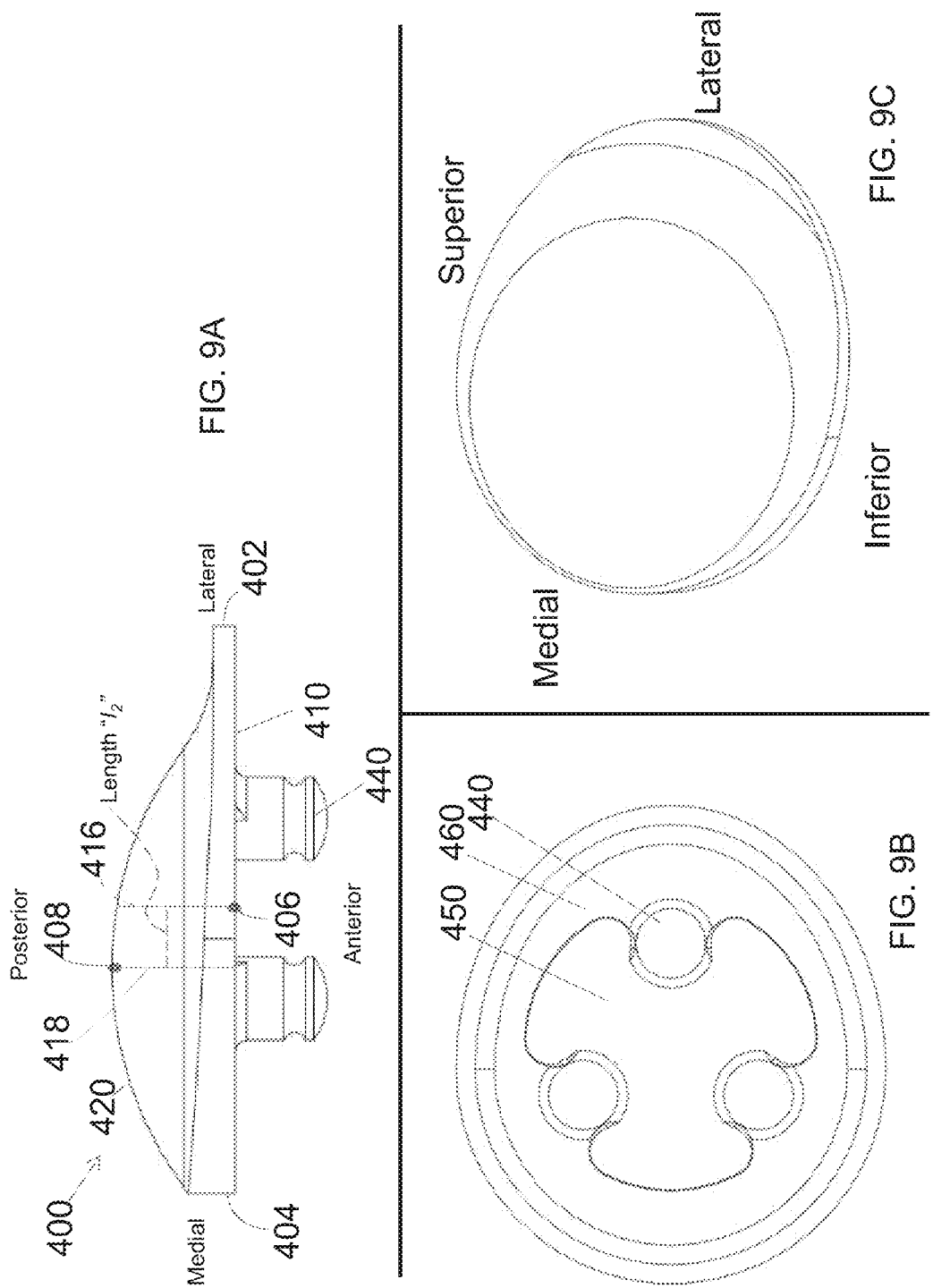

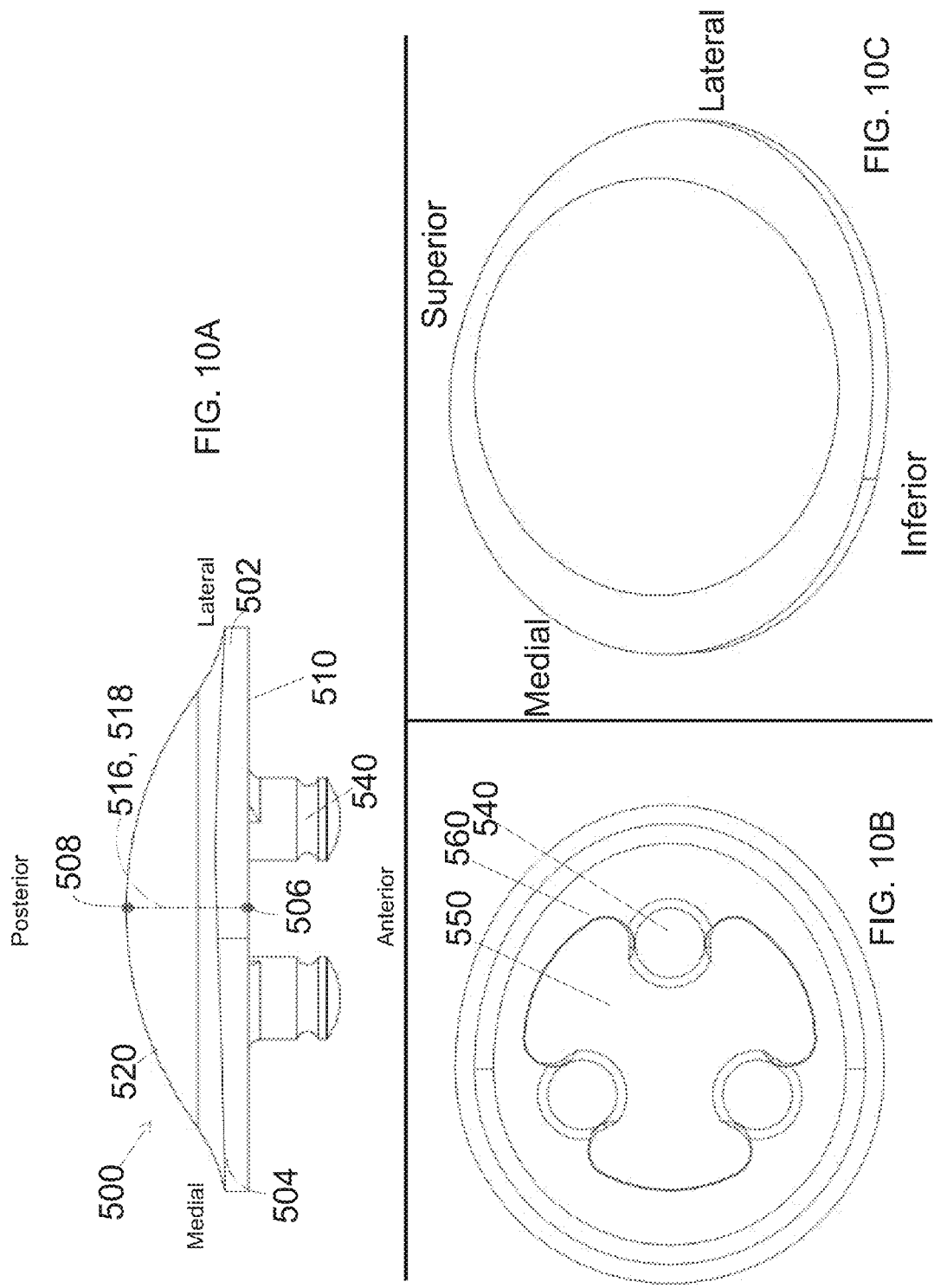

PATELLA IMPLANT SYSTEMS AND PATELLA TRIALS FOR SELECTING SAME

RELATED APPLICATION

This application claims the benefit of and priority to U.S. Provisional Application Ser. No. 61/731,150, filed Nov. 29, 2012, the entirety of this application is hereby incorporated herein by reference.

BACKGROUND

In total knee arthroplasty (TKA), appropriately designed prostheses and surgical techniques can help prevent postoperative complications related to the patella. However, several factors, such as the patella width-to-height ratio and the mediolateral position of the patella implant with respect to the resected patella, have clinical implications for TKA recovery, Anthropometric studies have established the mediolateral width of a patella is generally larger than its height, with the average width-to-height ratio around 1.25 (ranging from 0.8 to 1.6) regardless of gender or race, Most operative techniques recommend the patella implant be placed at the medial margin of the resected patella to help achieve appropriate tracking.

SUMMARY

The embodiments disclosed herein relate to patella implant systems and patella trials for selecting same, and more particularly to patella implant systems that allow independent adjustment of patella-femoral articulation and optimal coverage of the resected patella.

According to aspects illustrated herein, there is disclosed a patella trial that includes a baseplate having a medial-lateral axis and a superior-inferior axis; and a mobile articular surface member in direct physical contact with the baseplate and configured to move along at least one of the medial-lateral axis or the superior-inferior axis of the baseplate, wherein the baseplate has a bottom surface configured to temporarily attach to a resected patella, and wherein the baseplate has a top surface having at least one marking defining at least one of a medial-lateral offset or a superior-inferior offset of the articular surface member. In an embodiment, the baseplate has an anatomical, non-circular shape, enabling size selection based on width-to-height ratio, optimizing resected patella coverage. The mobile articular surface member is configured to move relative to the anatomical baseplate according to at least one degree of freedom allowing for mediolateral adjustment and/or superiorinferior adjustment to properly adjust position relative to a trochlea groove of a femoral prosthesis or the natural femur. In an embodiment, the mobile articular surface member is able to move relative to the anatomical baseplate according to one degree of freedom. In an embodiment, the mobile articular surface member is able to move relative to the anatomical baseplate according to two degrees of freedom.

According to aspects illustrated herein, there is disclosed a system that includes a patella trial comprising: a baseplate having a medial-lateral axis and a superior-inferior axis; and a mobile articular surface member in direct physical contact with the baseplate and configured to move along at least one of the medial-lateral axis or the superior-inferior axis of the baseplate, wherein the baseplate has a bottom surface configured to temporarily attach to a resected patella, and wherein the baseplate has a top surface having at least one marking defining at least one of a medial-lateral offset or a superior-inferior offset of the articular surface member relative to the baseplate; and an orthopaedic implant comprising: a one piece patella component having a posterior articular surface and a flat anterior surface having at least one fixation member extending outwardly therefrom, wherein the anterior surface has a medial/lateral width with a midpoint, wherein the posterior articular surface has a posterior-most point, wherein an imaginary line extending through the posterior-most point of the posterior articular surface is parallel to an imaginary line extending through the midpoint of the medial/lateral width of the anterior surface, and wherein a distance (I) is defined by measuring a length between the imaginary line extending through the posterior-most point and the imaginary line extending through the midpoint of the medial/lateral width; wherein the orthopaedic implant is selected from a set of orthopaedic implants each orthopaedic implant in the set having a different I, and wherein the chosen orthopaedic implant is selected based on the offset of the articular surface member relative to the baseplate on the patella trial.

According to aspects illustrated herein, there is disclosed a kit that includes a patella trial comprising: a baseplate having a medial-lateral axis and a superior-inferior axis; and a mobile articular surface member in direct physical contact with the baseplate and configured to move along at least one of the medial-lateral axis or the superior-inferior axis of the baseplate, wherein the baseplate has a bottom surface configured to temporarily attach to a resected patella, and wherein the baseplate has a top surface having at least one marking defining at least one of a medial-lateral offset or a superior-inferior offset of the articular surface member; a first orthopaedic implant comprising: a one piece patella component having a posterior articular surface and a flat anterior surface having at least one fixation member extending outwardly therefrom, wherein the anterior surface has a medial/lateral width with a midpoint, wherein the posterior articular surface has a posterior-most point, wherein an imaginary line extending through the posterior-most point of the posterior articular surface is parallel to an imaginary line extending through the midpoint of the medial/lateral width of the anterior surface, and wherein a first distance ($I_1$) is defined by measuring a length between the imaginary line extending through the posterior-most point and the imaginary line extending through the midpoint of the medial/lateral width; and a second orthopaedic implant comprising: a one piece patella component having a posterior articular surface and a flat anterior surface having at least one fixation member extending outwardly therefrom, wherein the anterior surface has a medial/lateral width with a midpoint, wherein the posterior articular surface has a posterior-most point, wherein an imaginary line extending through the posterior-most point of the posterior articular surface is parallel to an imaginary line extending through the midpoint of the medial/lateral width of the anterior surface, and wherein a second distance ($I_2$) is defined by measuring a length between the imaginary line extending through the posterior-most point and the imaginary line extending through the midpoint of the medial/lateral width; and wherein $I_1$ of the first orthopaedic implant is not equivalent to $I_2$ of the second orthopaedic implant.

According to aspects illustrated herein, a kit of the present invention includes different patella orthopaedic implant sizes, each available in different offsets relative to the outside profile, as depicted in Table 1. The selection of a patella orthopaedic implant from the kit is based on information obtained using a patella trial of the present disclosure. In an embodiment, the patella orthopaedic implants of the kit allow independent adjustment of patella-femoral articulation and optimal coverage of the resected patella. In an embodiment, because of the range of offsets, the locking peg(s) on the patella orthopaedic implants can be located where the patella is thickest. In an embodiment, the location of the peg(s) improves fixation by enabling the use of longer peg(s).

According to aspects illustrated herein, a kit of the present invention includes different patella orthopaedic implant sizes, each available in different offsets relative to the outside profile, as depicted in Table 2. The selection of a patella orthopaedic implant from the kit is based on information obtained using a patella trial of the present disclosure. In an embodiment, the patella orthopaedic implants of the kit allow independent adjustment of patella-femoral articulation and optimal coverage of the resected patella. In an embodiment, because of the range of offsets, the locking peg(s) on the prosthetic patella orthopaedic implants can be located where the patella is thickest. In an embodiment, the location of the pet(s) improves fixation by enabling the use of longer peg(s).

BRIEF DESCRIPTION OF THE DRAWINGS

The present invention will be further explained with reference to the attached drawings, wherein like structures are referred to by like numerals throughout the several views. The drawings shown are not necessarily to scale, with emphasis instead generally being placed upon illustrating the principles of the present invention.

FIG. 3A is a schematic of a human left patella viewed from a posterior aspect. FIGS. 3B-3C show removal of a portion of the patella articulation surface.

FIG. 4 is a schematic illustration demonstrating the templating of the resected patella from FIG. 3 to optimize resected patella coverage.

FIG. 5 is a schematic illustration demonstrating the drilling of holes into the resected patella from FIG. 3 for positioning pegs of a patella trial or a patella orthopaedic implant of the present invention.

FIG. 7A is a rear view of the patella trial of FIG. 6A, FIG. 7B is a schematic illustration demonstrating insertion of the patella trial of FIG. 6A on a resected patella for enabling size selection based on width-to-height ratio, optimizing resected patella coverage. A surgeon adjusts the mediolateral offset during the trial reduction using a patella trial of the present disclosure. After the trial reduction, the surgeon notes the information needed for the selection of the final patella implant: Appropriate size of the anatomical baseplate and appropriate value of the offset.

FIGS. 8A-8C show an embodiment of a monoblock patella orthopaedic size "+" implant of the present disclosure. The "+" indicates that the posterior articular surface has a medial offset.

FIGS. 9A-9C show an embodiment of a monoblock patella orthopaedic size "++" implant of the present disclosure. The "++" indicates that the posterior articular surface has a medial offset that is larger than the medial offset of the "+" size implant.

FIGS. 10A-10C show an embodiment of a monoblock patella orthopaedic size "0" implant of the present disclosure. The "0" indicates that the posterior articular surface is in a neutral position along the mediolateral axis.

While the above-identified drawings set forth presently disclosed embodiments, other embodiments are also contemplated, as noted in the discussion, This disclosure presents illustrative embodiments by way of representation and not limitation. Numerous other modifications and embodiments can be devised by those skilled in the art which fall within the scope and spirit of the principles of the presently disclosed invention.

DETAILED DESCRIPTION

Figure 1:
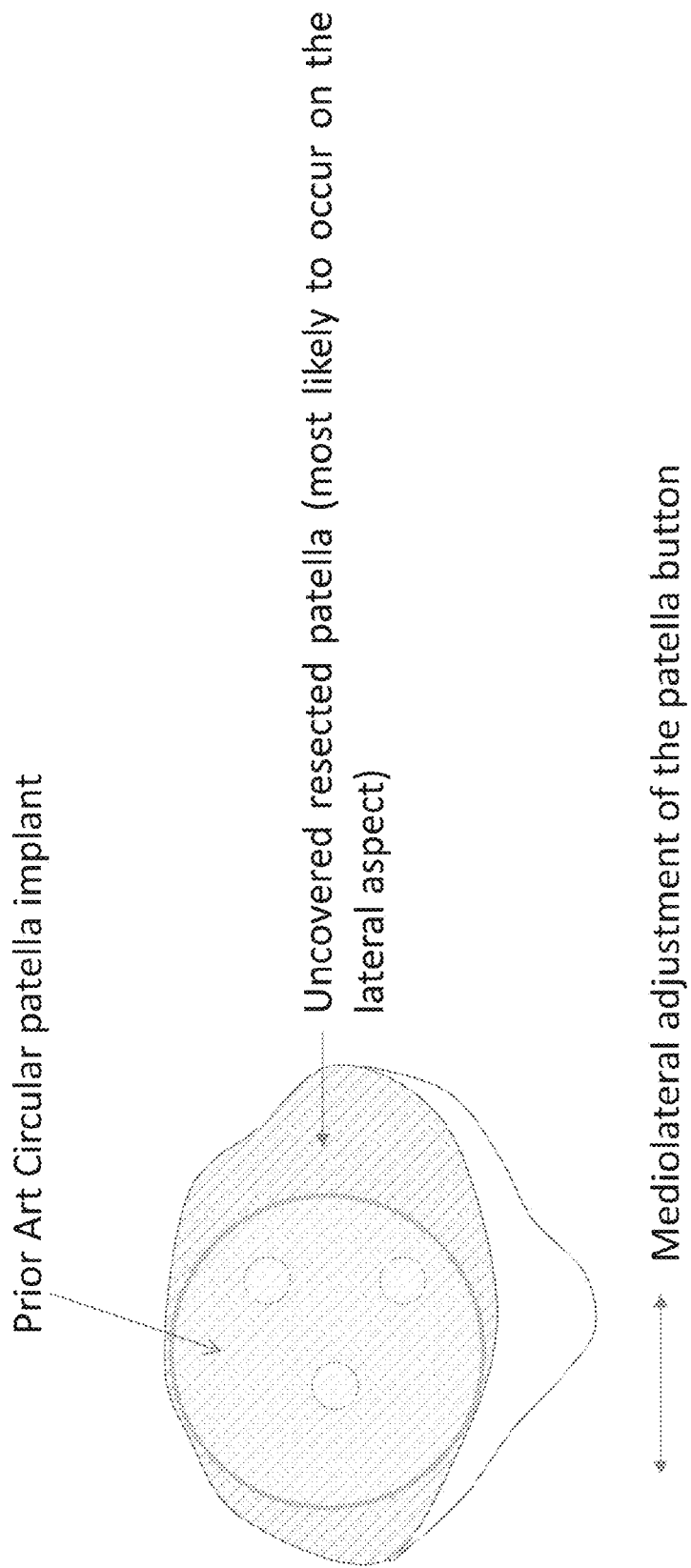
FIG. 1 is a schematic illustration demonstrating the advantages and disadvantages of a circular patella implant of the prior art.
Figure 2:
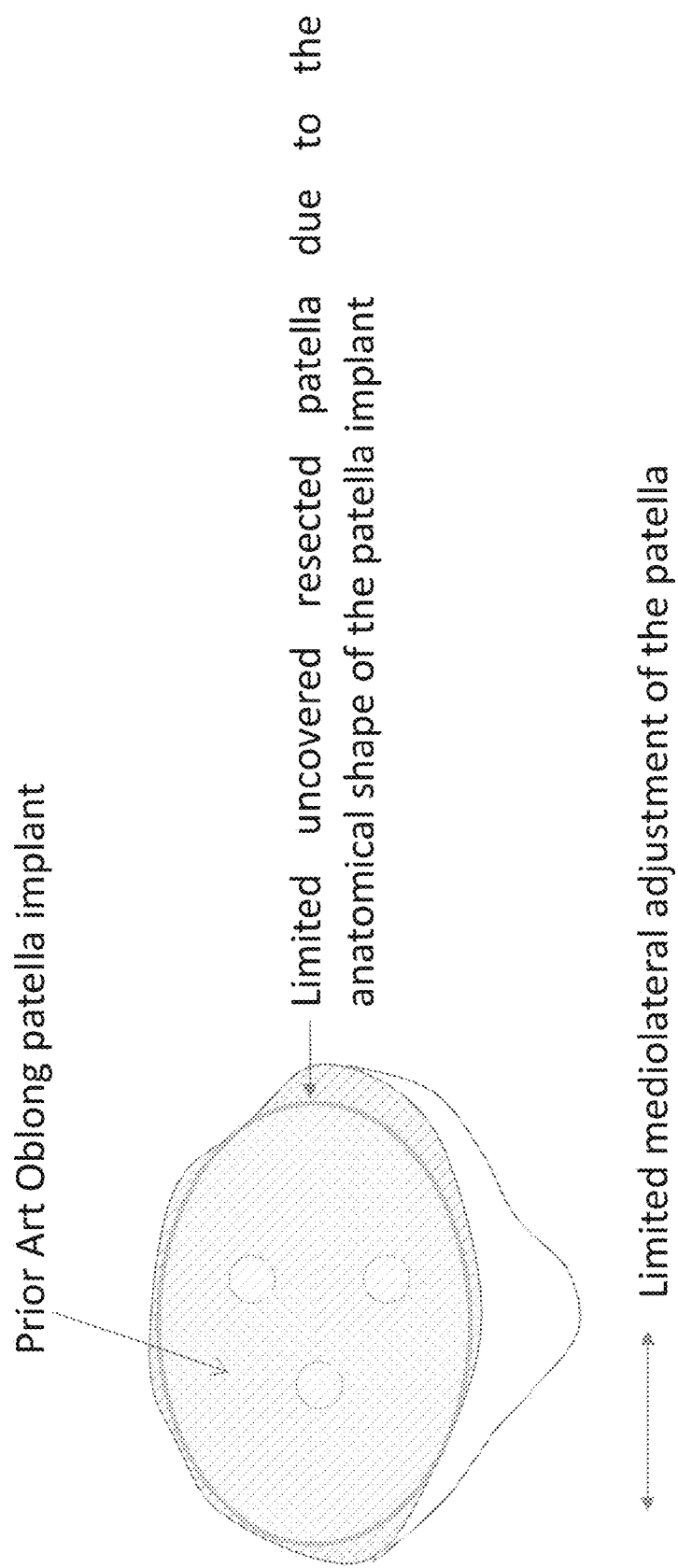
FIG. 2 is a schematic illustration demonstrating the advantages and disadvantages of an oblong patella implant of the prior art.

A conventional patella implant is typically circular in back and front views but may also be oblong. Furthermore, patella implants typically include one or more protrusions, or pegs, which are inserted into the natural patella and help firmly fix, typically with the addition of suitable adhesives, cements or other bonding materials, the implant and the remaining portion of the natural patella. A conventional patella implant includes a surface (hereinafter "upper surface") of any suitable design, typically, but not necessarily, substantially convex, and a planar, i.e., flat, undersurface. To surgically install such an implant, the natural patella is cut in planar, or flat, fashion and the implant is bonded, or otherwise fixed, (with or without the help of one or more pegs) to the newly cut face of the natural patella. In the minds of surgeons, conflict may exist regarding currently offered patella implants, natural patella shape, and the mediolateral patella implant placement. Surgeons tend to select circular patella implants by height, which leaves a portion of the resected patella uncovered along the mediolateral axis (usually the lateral aspect). On the other hand, a circular patella component can be shifted along the mediolateral axis to properly adjust position relative to the trochlea groove of a femoral prosthesis or the natural femur (see FIG. 1). Providing surgeons with an oblong patella implant enables size selection based on width-to-height ratio, optimizing resected patella coverage. However, the trade-off for optimum coverage is a loss of mediolateral adjustability, as doing so could result in implant overhang relative to the resected patella, a condition associated with poor clinical results (see FIG. 2).

In an embodiment, the present disclosure relates to patella trials intended to help surgeons identify proper offset. The anatomical profile is intended to provide optimum coverage of the resected patella, while the offset is intended to enable adjustment of the articular surface member's mediolateral position, superoinferior position, or both, relative to the trochlea groove of a femoral prosthesis or the natural femur. The patella trials feature an anatomical baseplate to be attached to the resected patella and a mobile articular surface component intended to move relative to the fixed baseplate. A series of markings provides information to the surgeon for helping determine optimum offset of the articular surface component. In an embodiment, the markings are etch marks. In an embodiment, the markings are laser marks. In an embodiment, the markings are raised marks. In an embodiment, the mobile articular surface member is dome-shaped. In an embodiment, the mobile articular surface member features one degree of freedom movement relative to the fixed baseplate (see FIGS. 6A and 6B). In an embodiment, the articular surface member features two degrees of freedom movement relative to the fixed baseplate (see FIGS. 13A-C).

The patella trials and implants of the present disclosure reconcile both resected patella coverage and mediolateral adjustability. In an embodiment, the present disclosure relates to a patella implant kit that includes a set of (two or more) patella implants featuring an anatomical outside profile available in several dimensions/sizes (i.e., width/height and thickness), similar to existing patella systems but with different offsets of the apex of the articular surface relative to one of the axes defining the anatomical shape (i.e., minor or major axes if the anatomical outside is non-circular), or with a combination of both. In an embodiment, a patella implant kit of the present disclosure includes a set of six implants to select from.

Figure 3B:
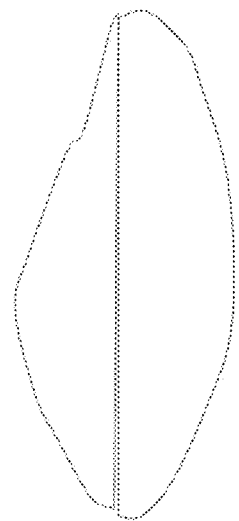
FIGS. 3A-3C are schematic illustrations demonstrating the preparation of a patella for a patella implant.
Figure 3C:
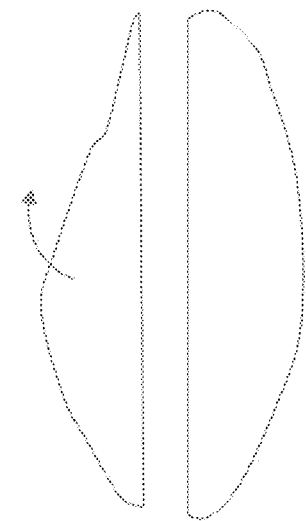
Figure 3A:
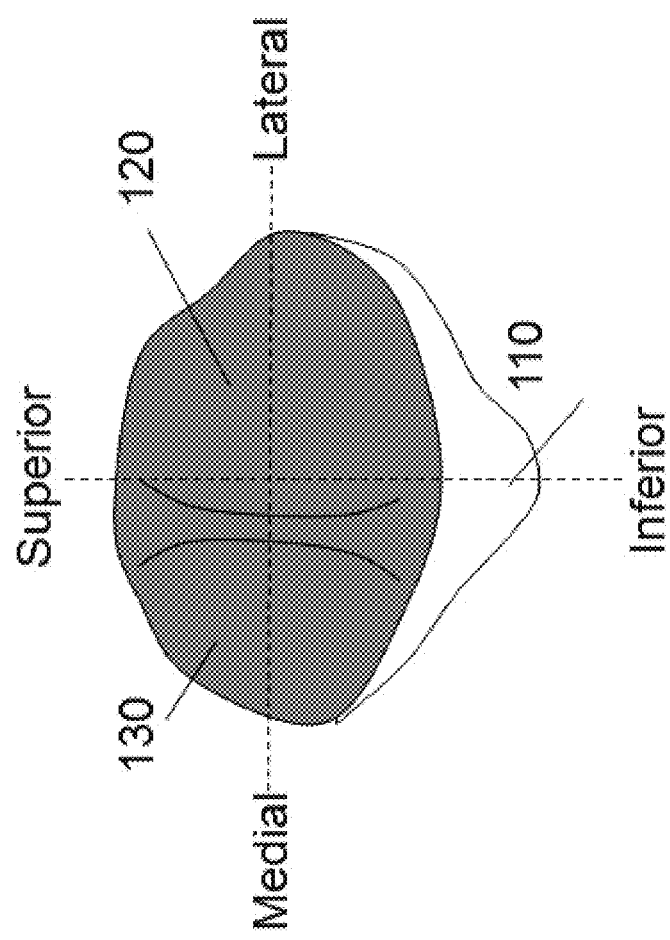

FIGS. 3A-3C are schematic illustrations demonstrating the preparation of a patella for a patella implant. Conventional in order to surgically repair a damaged patella 100 what is done is to remove a portion of the articulating surface 120/130 (the surface facing the knee joint) of the natural patella 100 leaving the connection between the natural patella and the muscle intact 110. The posterior surface has the articular facet, which is divided by a slightly marked longitudinal surface corresponding to the groove on the patellar surface of the femur. The larger lateral surface corresponds to the lateral condyle 120 and the smaller one 130, the medial condyle. The removal is typically effected using a vibrating saw or similar instrument.

Initially, a surgeon defines the appropriate implant size for optimum coverage of the resected patella. This can be performed by comparing the resected part of the native patella against templates, as illustrated in FIG. 4. In FIG. 4, for example, three sizes of the anatomical outside profile are available: sizes A, B and C. With the appropriate size selected (in this example, the Size B has been selected), the surgeon uses a patella guide to drill either a central hole or three peripheral holes, as illustrated in FIG. 5.

Figure 6A:
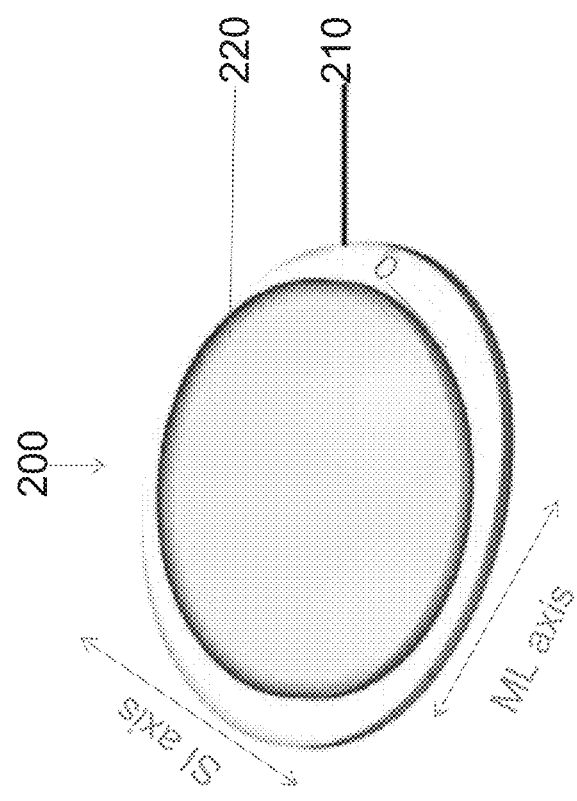
FIGS. 6A and 6B show an embodiment of a patella trial of the present disclosure. The patella trial features an anatomical baseplate and an articular surface member. The articular surface member is able to move relative to the anatomical baseplate according to one degree of freedom.
Figure 6B:
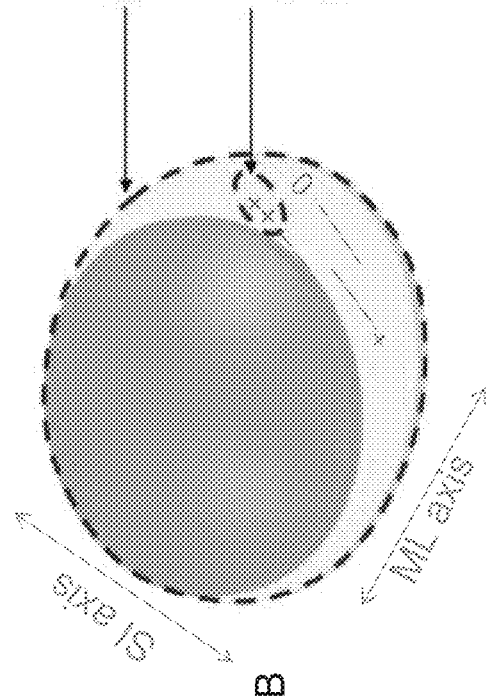

FIGS. 6A and 6B show an embodiment of a patella trial 200 of the present invention where one degree of freedom along the mediolateral (ML) axis is adjustable. Patella trial 200 includes an anatomical baseplate 210 having a medial-lateral axis and a superior-inferior axis and intended to cover the resected patella and a mobile articular member 220 intended to articulate against the patella groove of a femoral prosthesis or the natural femur (not represented) and configured to move along at least one of the medial-lateral axis or the superior-inferior axis of the baseplate. The anatomical baseplate 210 is non-circular in shape enabling size selection based on width-to-height ratio, optimizing resected patella coverage. The mobile articular surface member 220 is able to move relative to the anatomical baseplate 210 according to at least one degree of freedom allowing for medial/lateral adjustment and/or superior/inferior adjustment to properly adjust position relative to a trochlea groove of a femoral prosthesis or the natural femur. Although FIG. 6B illustrates the articular surface member 220 moving in a medial direction along the mediolateral axis, it should be understood that the patella trial 200 can be configured so that the articular surface member 220 moves in a lateral direction along the mediolateral axis.

FIG. 7A is a rear view of the patella trial 200 of FIG. 6B. As illustrated, a bottom surface of the mobile articular surface member 220 includes a mechanism 230 for irremovably attaching, and selective movement of the mobile articular surface member 220 to anatomical baseplate 210 in accordance with an illustrative embodiment of the invention. The close-up expanded view of the mechanism 230 shows that the mechanism 230 includes a shaft 232 and a shoulder 234 configured for insertion through an opening 215 in the baseplate 210. Since shoulder 234 is larger than the opening 215, shoulder 234 secures the mobile articular surface member 220 to the baseplate 210. Since the diameter of the shaft 232 is smaller than opening 215 along the medial-lateral axis, mobile articular surface member 220 is able to move along the medial-lateral axis of the anatomical baseplate 210 according to one degree of freedom.

A bottom surface of the baseplate 210 includes one or more pegs 240 which are preferably either cylindrical or rectangular, but which can be any other geometrical shape. Pegs 240 may be of any suitable size. Pegs 240 may be formed with circumferential depressions to help improve the bonding and anchorage by providing enhanced friction and further providing space in which adhesives and the like can accumulate. Pegs 240 are dimensioned to fit into holes prepared in the natural patella following the reaming of the bony patella during the preparation of the bony patella. A top surface of the baseplate 210 includes markings defining at least one of a medial-lateral offset or a superior-inferior offset of the mobile articular surface member 220. In an embodiment, the markings are etch marks. In an embodiment, the markings are laser marks. In an embodiment, the markings are raised marks.

FIG. 7B is a schematic illustration demonstrating insertion of the patella trial of FIG. 6A on a resected patella for enabling size selection based on width-to-height ratio, optimizing resected patella coverage. A surgeon adjusts the mediolateral offset during the trial reduction using a patella trial of the present disclosure. After the trial reduction, the surgeon notes the information needed for the selection of the final patella implant: Appropriate size of the anatomical baseplate and appropriate value of the offset.

A number of different combination patella orthopaedic implants may be molded in advance for each possible combination of baseplate size and articular surface member offset of the patella trial 200 of the present invention. FIGS. 8A-8C show an embodiment of a monoblock patella orthopaedic size "+" implant 300 of the present disclosure. The orthopaedic implant 300 features a high offset of the posterior articular surface 320 relative to the anatomical outside profile. The orthopaedic implant 300 also includes a flat anterior surface 310 having a number of fixation members, such as pegs 340, extending away therefrom. The pegs 340 are configured to be implanted into a surgically prepared posterior surface of the patient's natural patella. Bone cement 350 can be applied to the cement pockets 360 in the underside of the flat anterior surface 310.

The posterior articular surface 320 has a dome-shaped surface. A point 308 on the dome-shaped surface defines the posterior-most point of the orthopaedic implant 300. As can be seen in FIG. 8A, an imaginary line 318 extending through the posterior-most point 308 of the posterior articular surface 320 is parallel to an imaginary line 316 extending through a midpoint 306 of the medial/lateral width of the anterior surface 310 of the patella implant 300, but is spaced apart from it in the medial direction. A distance ($I_1$) is defined by measuring a length between the imaginary line 318 extending through the posterior-most point 308 and the imaginary line 316 extending through the midpoint 306 of the medial/lateral width. Imaginary lines 316 and 318 are perpendicular to flat anterior surface 310. Although FIGS. 8A and 8C illustrate the posterior-most point 308 of the posterior articular surface 320 offset in a medial direction along the mediolateral axis, it should be understood that the orthopaedic implant 300 can be configured so that the posterior-most point 308 of the posterior articular surface 320 is offset by a similar distance $I_1$ in a lateral direction along the mediolateral axis.

FIGS. 9A-9C show an embodiment of a monoblock patella orthopaedic size "++" implant 400 of the present disclosure. The orthopaedic implant 400 features a high offset of the posterior articular surface 420 relative to the anatomical outside profile. The orthopaedic implant 400 also includes a flat anterior surface 410 having a number of fixation members, such as pegs 440, extending away therefrom. The pegs 440 are configured to be implanted into a surgically prepared posterior surface of the patient's natural patella. In such a way, the posterior articular surface 420 of the orthopaedic implant 400 faces toward the femur thereby allowing the posterior articular surface 420 to articulate with the femoral condyles during flexion and extension of the patient's knee. The posterior articular surface 420 is sufficiently designed to articulate against the natural distal femur or a prosthetic distal femur. Bone cement 450 can be applied to the cement pockets 460 in the underside of the flat anterior surface 410.

The posterior articular surface 420 has a dome-shaped surface. A point 408 on the dome-shaped surface defines the posterior-most point of the orthopaedic implant 400. As can be seen in FIG. 9A, an imaginary line 418 extending through the posterior-most point 408 of the posterior articular surface 420 is parallel to an imaginary line 416 extending through a midpoint 406 of the medial/lateral width of the anterior surface 410 of the patella implant 400, but is spaced apart from it in the medial direction. A distance ($I_2$) is defined by measuring a length between the imaginary line 418 extending through the posterior-most point 408 and the imaginary line 416 extending through the midpoint 406 of the medial/lateral width. Imaginary lines 416 and 418 are perpendicular to flat anterior surface 410. Although FIGS. 9A and 9C illustrate the posterior-most point 408 of the posterior articular surface 420 offset in a medial direction along the mediolateral axis, it should be understood that the orthopaedic implant 400 can be configured so that the posterior-most point 408 of the posterior articular surface 420 is offset by a similar distance $I_2$ in a lateral direction along the mediolateral axis.

FIGS. 10A-10C show an embodiment of a monoblock patella orthopaedic size "0" implant 500 of the present disclosure. The orthopaedic implant 500 features a high offset of the posterior articular surface 520 relative to the anatomical outside profile. The orthopaedic implant 500 also includes a flat anterior surface 510 having a number of fixation members, such as pegs 540, extending away therefrom. The pegs 540 are configured to be implanted into a surgically prepared posterior surface of the patient's natural patella. In such a way, the posterior articular surface 520 of the orthopaedic implant 500 faces toward the femur thereby allowing the posterior articular surface 520 to articulate with the femoral condyles during flexion and extension of the patient's knee. The posterior articular surface 520 is sufficiently designed to articulate against the natural distal femur or a prosthetic distal femur. Bone cement 550 can be applied to the cement pockets 560 in the underside of the flat anterior surface 510.

The posterior articular surface 520 has a dome-shaped surface. A point 508 on the dome-shaped surface defines the posterior-most point of the orthopaedic implant 500. As can be seen in FIG. 10A, an imaginary line 518 extending through the posterior-most point 508 of the posterior articular surface 520 overlaps an imaginary line 516 extending through a midpoint 506 of the medial/lateral width of the anterior surface 510 of the patella implant 500. Since the imaginary line 516 extending through the midpoint 506 and the imaginary line 518 extending through the posterior-most point 508 overlap one another, there is no offset of the posterior articular surface 520 along the medial-lateral axis of the flat anterior surface 510. Imaginary lines 516 and 518 are perpendicular to flat anterior surface 510.

The monoblock patella orthopaedic implants illustrated in FIGS. 8A, 9A and 10A, all have different values for I. $I_1$ of monoblock patella orthopaedic size "+" implant 300 is smaller than I, of monoblock patella orthopaedic size "++"

implant 400. I3 of monoblock patella orthopaedic size "0" implant 500 is equal to the value 0.

A patella orthopaedic implant of the present invention is embodied as a monolithic polymer body constructed with a material that allows for smooth articulation between the patella orthopaedic implant and the femur. A patella trial or a patella orthopaedic implant of the present disclosure may be formed of biocompatible materials such as various polymers including ultra-high molecular weight polyethylene, ceramic materials and metals such as stainless steel, titanium and cobalt chrome alloys. The bone contacting side of a patella trial or a patella orthopaedic implant in accordance with the present invention may include bone ingrowth promoting material such as trabecular metal to facilitate securement of the patellar prosthesis to the patella.

The surgeon selects the appropriate monoblock patella orthopaedic implant (300, 400 or 500, for example) from a set of patella orthopaedic implants of the present invention, which is defined by the size of the anatomical outside profile (first parameter) and the dome-shaped articular surface offset relative to the anatomical outside profile (second parameter) in order to duplicate the geometry of the patella trial. Table I lists different patella orthopaedic implants of the present invention assuming 6 anatomical sizes available under 3 offset options, resulting in 18 monoblock patella orthopaedic implants (i.e., 6×3). More generally, a kit available under (m) sizes, each available under (n) offset options will result in (m*n) monoblock patella implants.

TABLE 1

| Size   | A      | B      | C      | D      | E      | F      |
|--------|--------|--------|--------|--------|--------|--------|
| Offset | 0 + ++ | 0 + ++ | 0 + ++ | 0 + ++ | 0 + ++ | 0 + ++ |

Figure 11:
FIG. 11 shows a set of monoblock patella orthopaedic implants of the present invention, namely a size "0", "+" and "++" mediolateral offset and three sizes of anatomical outside profiles, namely a size "A", "B" and "C" to yield a total of nine (9) monoblock patella orthopaedic implants of the present invention.

FIG. 11 shows a set of monoblock patella orthopaedic implants 300, 400 and 500 of the present invention having three sizes of anatomical outside profiles, namely a 35 mm (size "A"), 38 mm (size "B") and 41 mm (size "C"), to yield a total of nine (9) monoblock patella orthopaedic implants of the present invention. As noted above, other sizes are contemplated and within the spirit of the invention.

Figure 12:
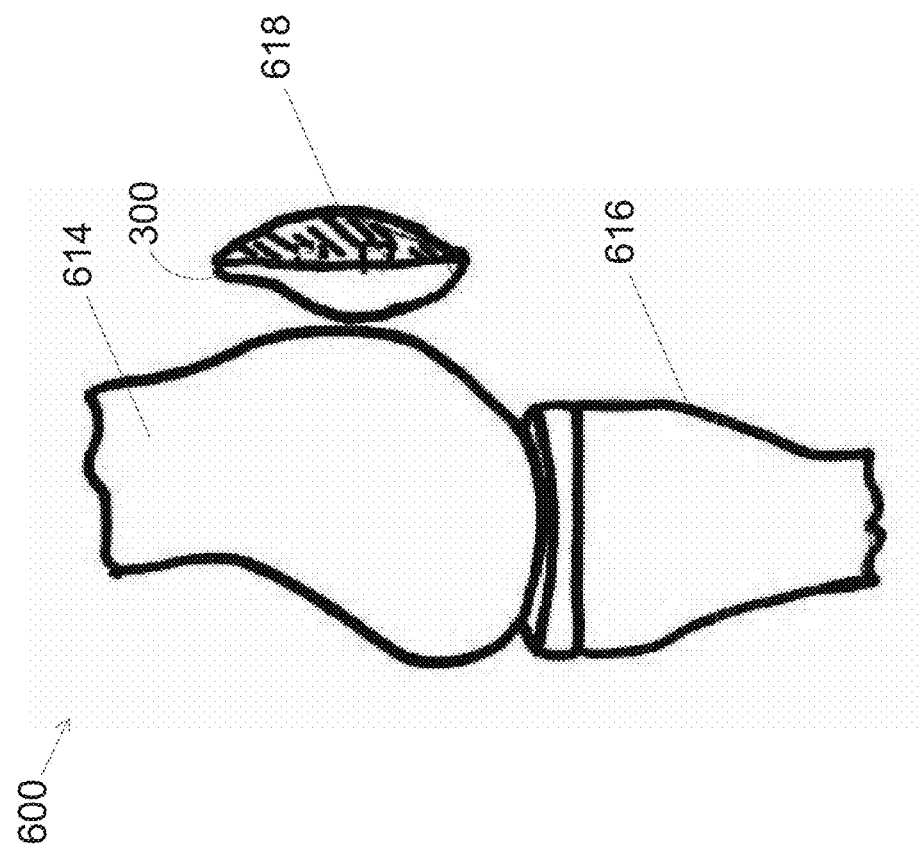
FIG. 12 is a diagrammatic lateral side showing a patella implant of the present invention in a knee joint.

FIG. 12 is a largely diagrammatic lateral side view showing a monoblock patella orthopaedic implant of the present invention (such as implant 300) in a knee joint 600. A distal femur 614 and a proximal tibia 616 can be prepared for the reception a femoral component and a tibial component. Once a portion of the patella has been removed, a patella orthopaedic implant 300 may be fixed to the remaining portion of the natural patella by some suitable means. Attachment of the implant 300 to the natural patella may be effected with cement 350 and/or through use of pegs 340. The implant 300 is shaped to slidably fit within the groove, of equivalent, of the corresponding natural or prosthetic lower end of the femur, depending on whether the natural lower femur is to remain or be replaced, respectively. In such a way, the posterior articular surface 320 of the patella orthopaedic implant 300 faces toward the femur thereby allowing the posterior articular surface 320 to articulate with the femoral condyles during flexion and extension of the patient's knee. The posterior articular surface 320 is sufficiently designed to articulate against the natural distal femur or a prosthetic distal femur.

Figure 13:
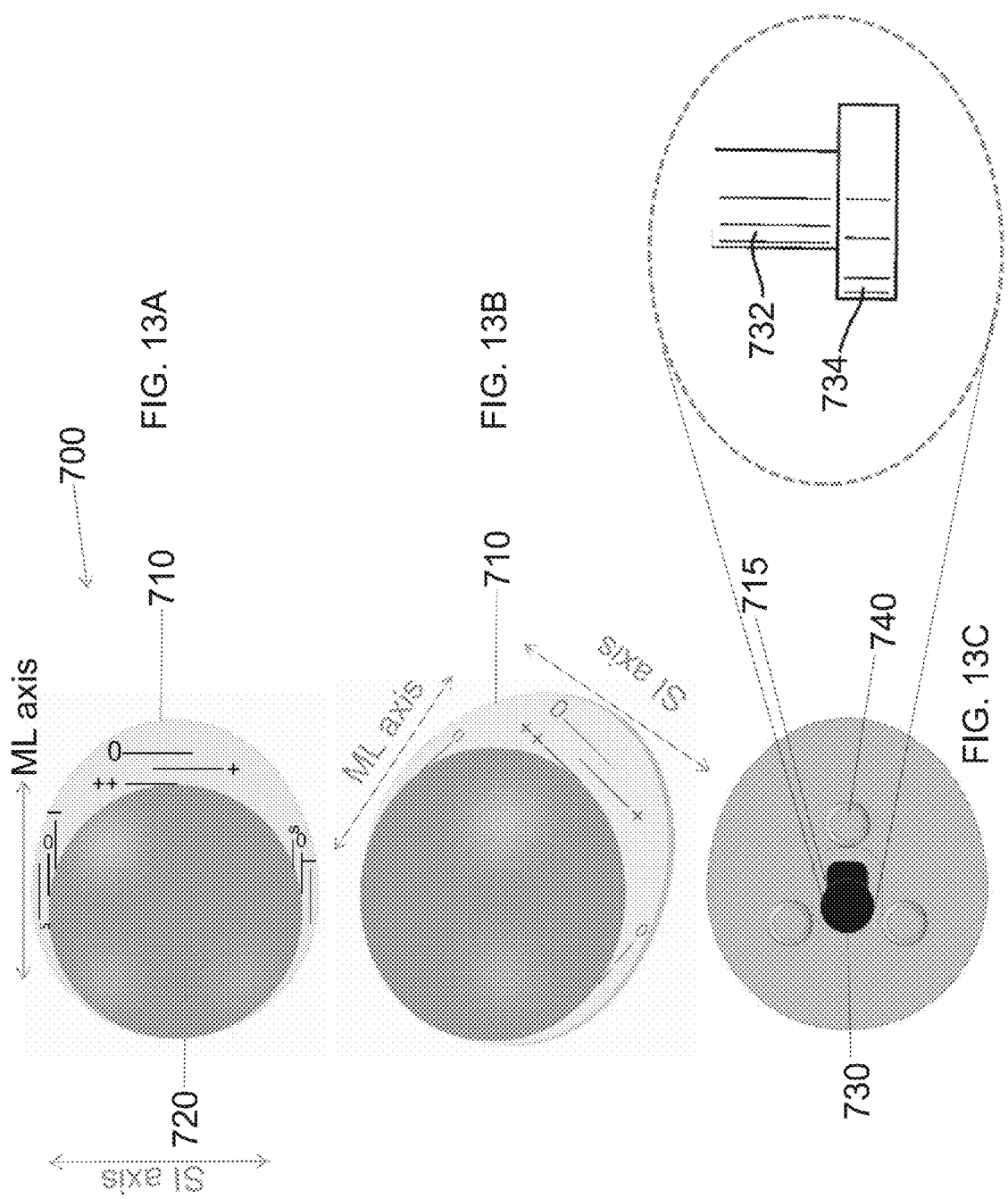
FIGS. 13A-13C show an embodiment of a patella trial of the present disclosure. The patella trial features an anatomical baseplate and an articular surface member. The articular surface member is able to move relative to the anatomical baseplate according to two degrees of freedom.

FIGS. 13A-13C show an embodiment of a patella trial 700 of the present invention where two degrees of freedom along the mediolateral (ML) and the superiorinferior (SI) axes are adjustable. Patella trial 700 includes an anatomical baseplate 710 having a medial-lateral axis and a superior-inferior axis and intended to cover the resected patella and a mobile articular member 720 intended to articulate against the patella groove of the femoral component (not represented) and configured to move along the medial-lateral axis and the superior-inferior axis of the baseplate. The anatomical baseplate 710 is non-circular in shape enabling size selection based on width-to-height ratio, optimizing resected patella coverage. In this embodiment, the position of the mobile articular member 720 relative to the anatomical baseplate 710 can be adjusted according to two degrees of freedoms (e.g., along the mediolateral axis as well as the superoinferior axis).

FIG. 13C is a rear view of the patella trial of FIG. 13B. As illustrated, a bottom surface of the mobile articular surface member 720 includes a mechanism 730 for irremovably attaching, and selective movement of, the mobile articular surface member 720 to anatomical baseplate 710 in accordance with an illustrative embodiment of the invention. The close-up expanded view of the mechanism 730 shows that the mechanism 730 includes a shaft 732 and a shoulder 734 configured for insertion through an opening 715 in the baseplate 710. Since shoulder 734 is larger than the opening 715, shoulder 734 secures the mobile articular surface member 720 to the baseplate 710. Since the diameter of the shaft 732 is smaller than opening 715 along both the medial-lateral axis and the superior-inferior axis, mobile articular surface member 720 is able to move along both the medial-lateral and superior-inferior axes of the anatomical baseplate 710 according to two degrees of freedom.

A bottom surface of the baseplate 710 includes one or more pegs 740 which are preferably either cylindrical or rectangular, but which can be any other geometrical shape. Pegs 740 may be of any suitable size. Pegs 740 may be formed with circumferential depressions to help improve the bonding and anchorage by providing enhanced friction and further providing space in which adhesives and the like can accumulate. Pegs 740 are dimensioned to fit into holes prepared in the natural patella following the reaming of the bony patella during the preparation of the bony patella.

A top surface of the baseplate 710 includes markings defining both a medial-lateral offset and a superior-inferior offset of the mobile articular surface member 720. The markings on the baseplate 710 defining the medial-lateral offset are: "0" (neutral), "+" and "++". The markings on the baseplate 710 defining the superior-inferior offset are "0" (neutral), "S" and "I". In an embodiment, the markings are etch marks. In an embodiment, the markings are laser marks. In an embodiment, the markings are raised marks.

A number of different combination patella orthopaedic implants may be molded in advance for each possible combination of baseplate size and articular surface member offset of the patella trial 700 of the present invention.

FIGS. 14A-14D show an embodiment of a monoblock patella orthopaedic size "+ ML, 0 SI" implant 800 of the present disclosure. The orthopaedic implant 800 features a high offset of the posterior articular surface 801 relative to the anatomical outside profile. The orthopaedic implant 800 also includes a flat anterior surface 802 having a number of fixation members, such as pegs 803, extending away therefrom. The pegs 803 are configured to be implanted into a surgically prepared posterior surface of the patient's natural patella. Bone cement 805 can be applied to the cement pockets 806 in the underside of the flat anterior surface 802.

Figure 14:
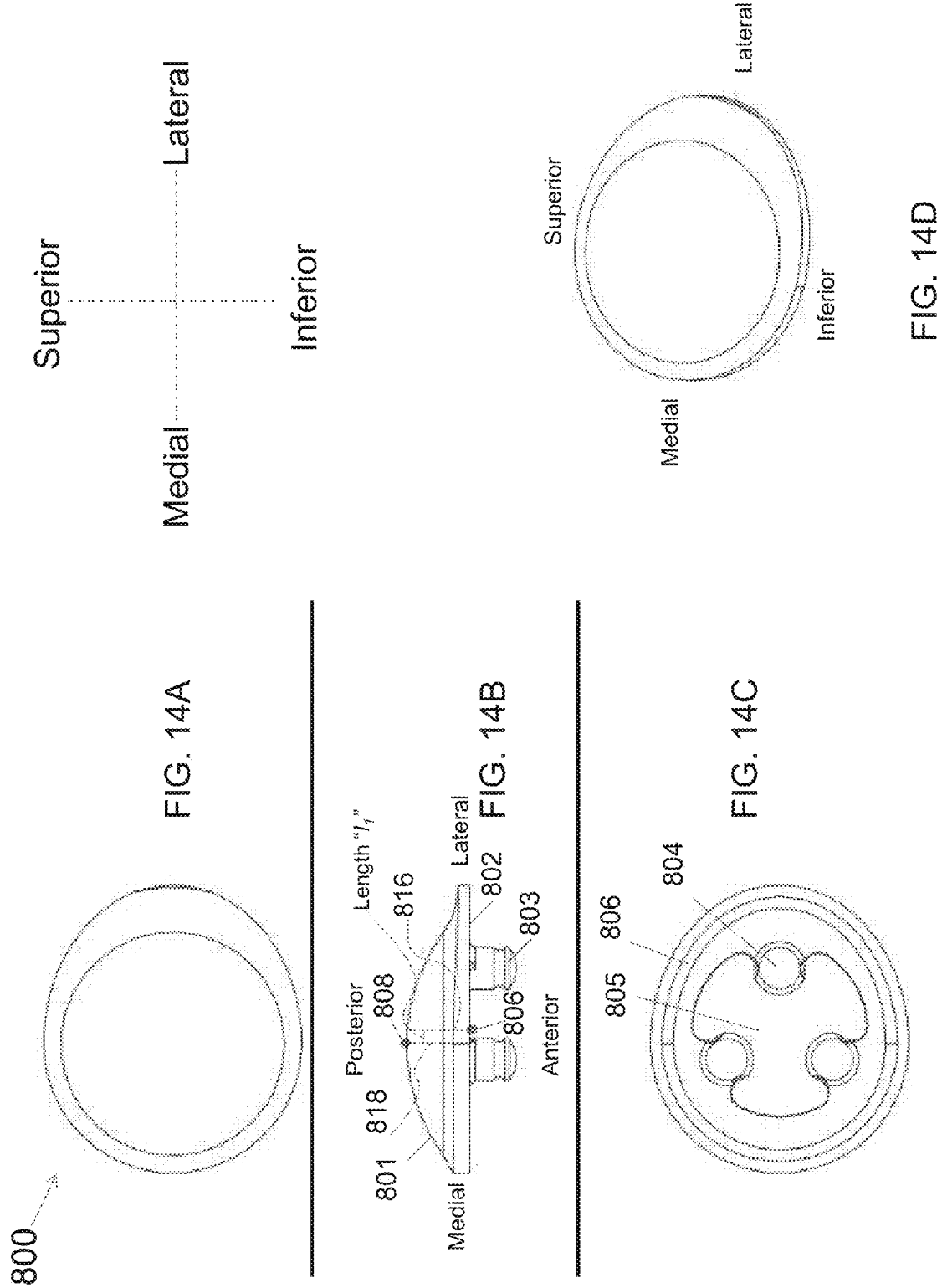
FIGS. 14A-14D show an embodiment of a monoblock patella orthopaedic implant being offset in the medial direction along the medial-lateral axis, and in a neutral position along the superior-inferior axis. This implant is referred to as a size "+ML, 0 SI" implant.

The posterior articular surface 801 has a dome-shaped surface. A point 808 on the dome-shaped surface defines the posterior-most point of the orthopaedic implant 800. As can be seen in FIG. 14B, an imaginary line 818 extending through the posterior-most point 808 of the posterior articular surface 801 is parallel to an imaginary line 816 extending through a midpoint 806 of the medial/lateral width of the anterior surface 802 of the patella implant 800, but is spaced apart from it in the medial direction. A distance ($I_1$) is defined by measuring a length between the imaginary line 818 extending through the posterior-most point 808 and the imaginary line 816 extending through the midpoint 806 of the medial/lateral width. Imaginary lines 816 and 818 are perpendicular to flat anterior surface 802. Although FIGS. 14B and 14D illustrate the posterior-most point 808 of the posterior articular surface 801 offset in a medial direction along the mediolateral axis, it should be understood that the orthopaedic implant 800 can be configured so that the posterior-most point 808 of the posterior articular surface 801 is offset by a similar distance $I_1$ in a lateral direction along the mediolateral axis.

FIGS. 15A-15D show an embodiment of a monoblock patella orthopaedic size "+ ML, I SI" implant 810 of the present disclosure. The orthopaedic implant 810 features a high offset of the posterior articular surface 801 relative to the anatomical outside profile. The orthopaedic implant 810 also includes a flat anterior surface 802 having a number of fixation members, such as pegs 803, extending away therefrom. The pegs 803 are configured to be implanted into a surgically prepared posterior surface of the patient's natural patella. Bone cement 805 can be applied to the cement pockets 806 in the underside of the flat anterior surface 802.

Figure 15:
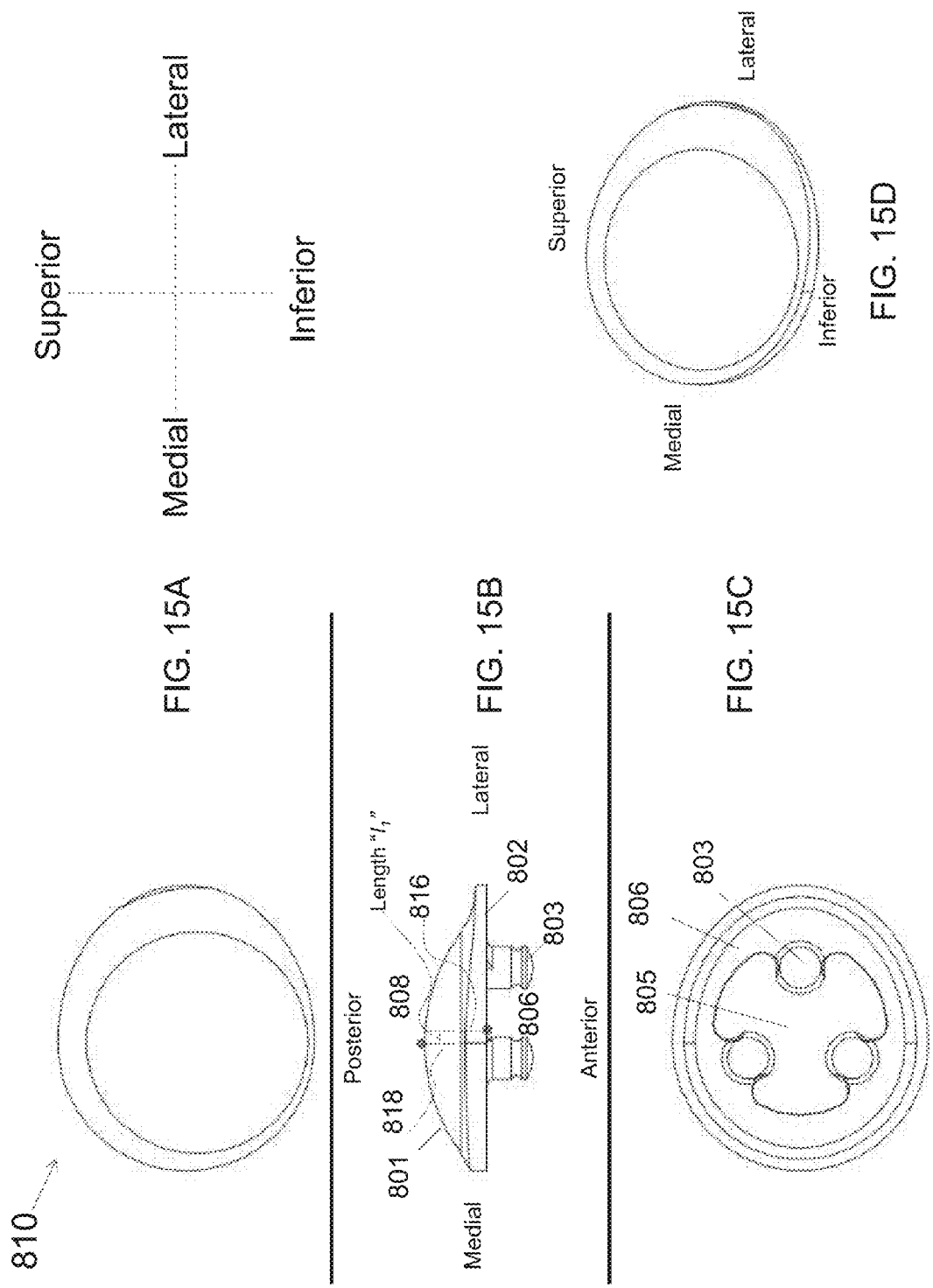
FIGS. 15A-15D show an embodiment of a monoblock patella orthopaedic implant being offset in the medial direction along the medial-lateral axis, and having an inferior offset along the superior-inferior axis. This implant is referred to as a size "+ML, I SI" implant.

The posterior articular surface 801 has a dome-shaped surface. A point 808 on the dome-shaped surface defines the posterior-most point of the orthopaedic implant 800. As can be seen in FIG. 15B, an imaginary line 818 extending through the posterior-most point 808 of the posterior articular surface 801 is parallel to an imaginary line 816 extending through a midpoint 806 of the medial/lateral width of the anterior surface 802 of the patella implant 810, but is spaced apart from it in the medial direction. A distance ($I_1$) is defined by measuring a length between the imaginary line 818 extending through the posterior-most point 808 and the imaginary line 816 extending through the midpoint 806 of the medial/lateral width. Imaginary lines 816 and 818 are perpendicular to flat anterior surface 802. Although FIGS. 15B and 15D illustrate the posterior-most point 808 of the posterior articular surface 801 offset in a medial direction along the mediolateral axis, it should be understood that the orthopaedic implant 810 can be configured so that the posterior-most point 808 of the posterior articular surface 801 is offset by a similar distance $I_1$ in a lateral direction along the mediolateral axis.

FIGS. 16A-16D show an embodiment of a monoblock patella orthopaedic size "+ ML, S SI" implant 820 of the present disclosure. The orthopaedic implant 820 features a high offset of the posterior articular surface 801 relative to the anatomical outside profile. The orthopaedic implant 820 also includes a flat anterior surface 802 having a number of fixation members, such as pegs 803, extending away therefrom. The pegs 803 are configured to be implanted into a surgically prepared posterior surface of the patient's natural patella. Bone cement 805 can be applied to the cement pockets 806 in the underside of the flat anterior surface 802.

Figure 16:
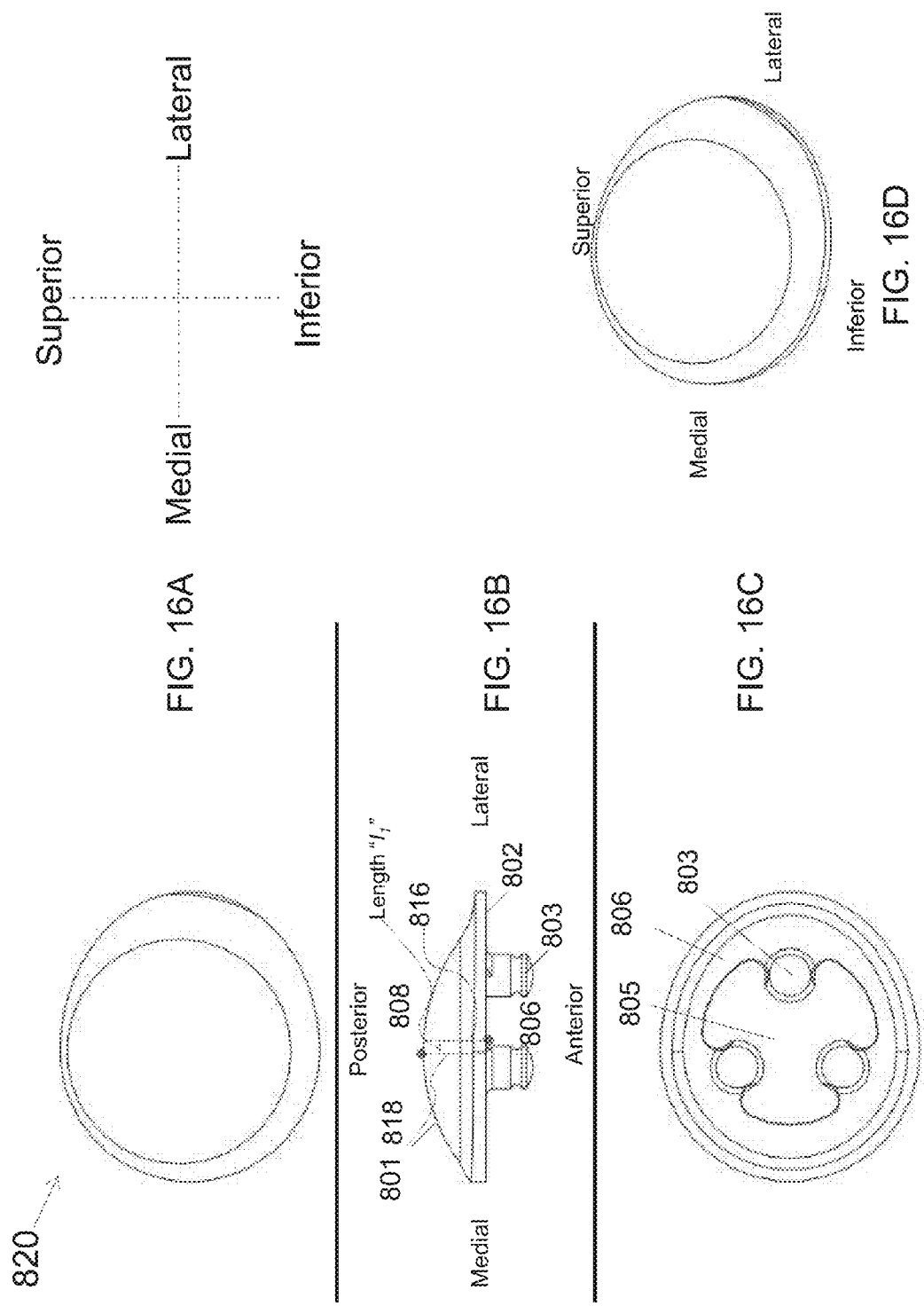
FIGS. 16A-16D show an embodiment of a monoblock patella orthopaedic implant being offset in the medial direction along the medial-lateral axis, and having a superior offset along the superior-inferior axis. This implant is referred to as a size "+ML, S SI" implant.

The posterior articular surface 801 has a dome-shaped surface. A point 808 on the dome-shaped surface defines the posterior-most point of the orthopaedic implant 820. As can be seen in FIG. 16B, an imaginary line 818 extending through the posterior-most point 808 of the posterior articular surface 801 is parallel to an imaginary line 816 extending through a midpoint 806 of the medial/lateral width of the anterior surface 802 of the patella implant 820, but is spaced apart from it in the medial direction. A distance ($I_1$) is defined by measuring a length between the imaginary line 818 extending through the posterior-most point 808 and the imaginary line 816 extending through the midpoint 806 of the medial/lateral width. Imaginary lines 816 and 818 are perpendicular to flat anterior surface 802. Although FIGS. 16B and 16D illustrate the posterior-most point 808 of the posterior articular surface 801 offset in a medial direction along the mediolateral axis, it should be understood that the orthopaedic implant 820 can be configured so that the posterior-most point 808 of the posterior articular surface 801 is offset by a similar distance $I_1$ in a lateral direction along the mediolateral axis.

FIGS. 17A-17D show an embodiment of a monoblock patella orthopaedic size "++ ML, 0 SI" implant 830 of the present disclosure. The orthopaedic implant 830 features a high offset of the posterior articular surface 801 relative to the anatomical outside profile. The orthopaedic implant 830 also includes a flat anterior surface 802 having a number of fixation members, such as pegs 803, extending away therefrom. The pegs 803 are configured to be implanted into a surgically prepared posterior surface of the patient's natural patella. In such a way, the posterior articular surface 801 of the orthopaedic implant 830 faces toward the femur thereby allowing the posterior articular surface 801 to articulate with the femoral condyles during flexion and extension of the patient's knee. The posterior articular surface 801 is sufficiently designed to articulate against the natural distal femur or a prosthetic distal femur. Bone cement 805 can be applied to the cement pockets 806 in the underside of the flat anterior surface 802.

Figure 17:
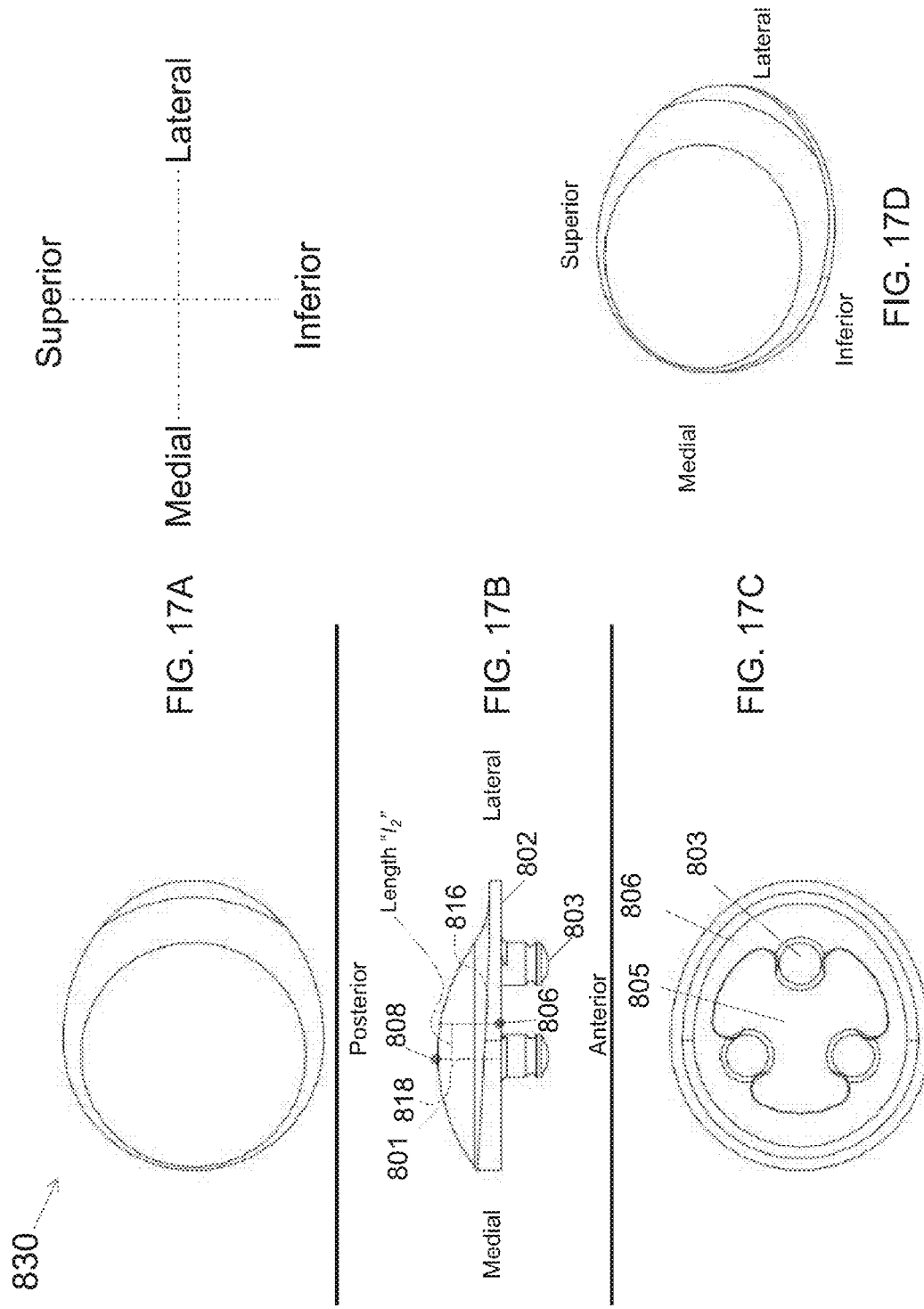
FIGS. 17A-17D show an embodiment of a monoblock patella orthopaedic implant being offset in the medial direction along the medial-lateral axis, and in a neutral position along the superior-inferior axis. This implant is referred to as a size "++ML, 0 SI" implant.

The posterior articular surface 801 has a dome-shaped surface. A point 808 on the dome-shaped surface defines the posterior-most point of the orthopaedic implant 830. As can be seen in FIG. 17B, an imaginary line 818 extending through the posterior-most point 808 of the posterior articular surface 801 is parallel to an imaginary line 816 extending through a midpoint 806 of the medial/lateral width of the anterior surface 802 of the patella implant 830, but is spaced apart from it in the medial direction. A distance ($I_2$) is defined by measuring a length between the imaginary line 818 extending through the posterior-most point 808 and the imaginary line 816 extending through the midpoint 806 of the medial/lateral width. Imaginary lines 816 and 818 are perpendicular to flat anterior surface 802. Although FIGS. 17B and 17D illustrate the posterior-most point 808 of the posterior articular surface 801 offset in a medial direction along the mediolateral axis, it should be understood that the orthopaedic implant 830 can be configured so that the posterior-most point 808 of the posterior articular surface 801 is offset by a similar distance $I_2$ in a lateral direction along the mediolateral axis.

FIGS. 18A-18D show an embodiment of a monoblock patella orthopaedic size "++ ML, I SI" implant 840 of the present disclosure. The orthopaedic implant 840 features a high offset of the posterior articular surface 801 relative to the anatomical outside profile. The orthopaedic implant 840 also includes a flat anterior surface 802 having a number of fixation members, such as pegs 803, extending away therefrom. The pegs 803 are configured to be implanted into a surgically prepared posterior surface of the patient's natural patella. in such a way, the posterior articular surface 801 of the orthopaedic implant 840 faces toward the femur thereby allowing the posterior articular surface 801 to articulate with the femoral condyles during flexion and extension of the patient's knee. The posterior articular surface 801 is sufficiently designed to articulate against the natural distal femur or a prosthetic distal femur. Bone cement 805 can be applied to the cement pockets 806 in the underside of the flat anterior surface 802.

Figure 18:
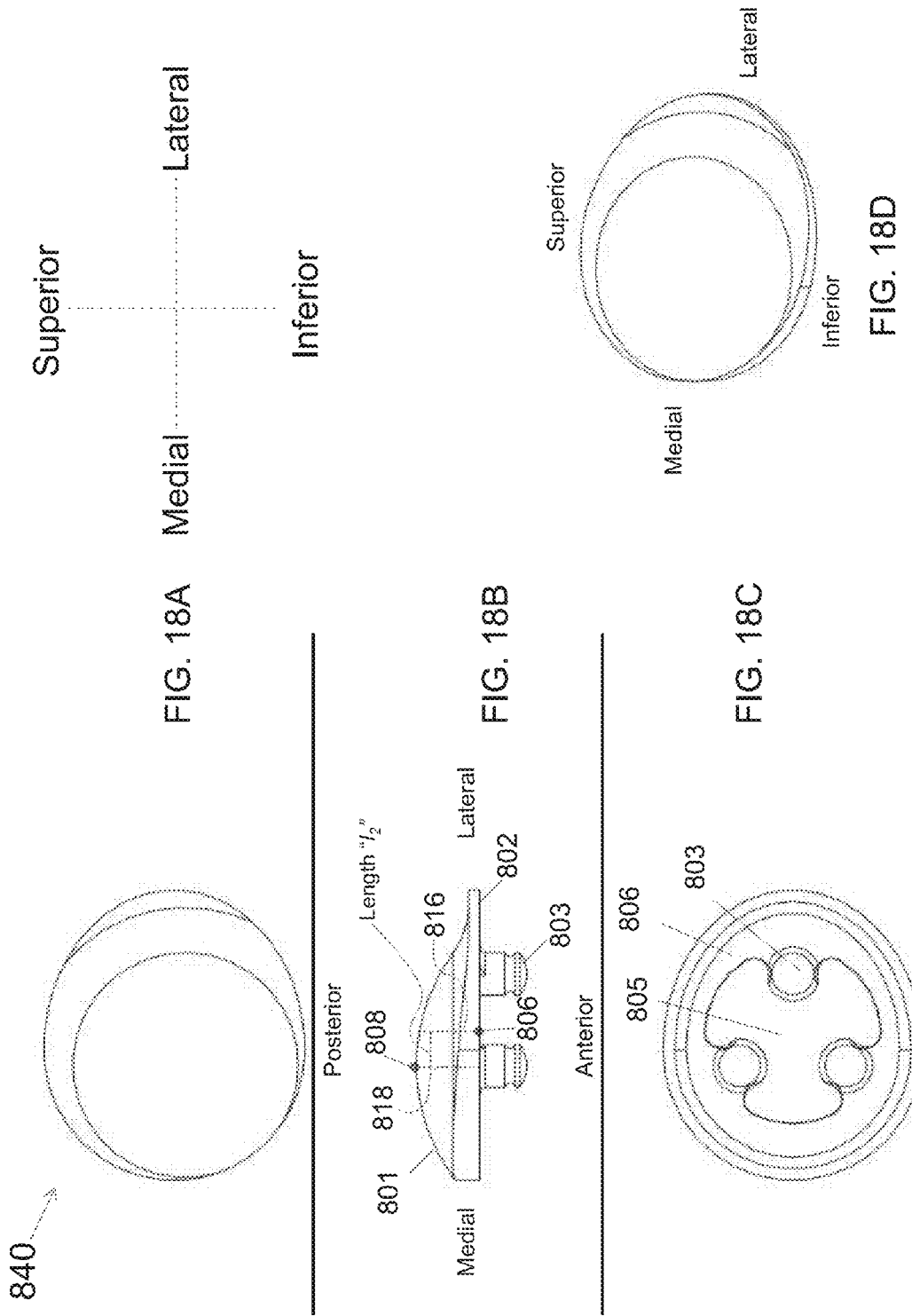
FIGS. 18A-18D show an embodiment of a monoblock patella orthopaedic implant being offset in the medial direction along the medial-lateral axis, and having an inferior offset along the superior-inferior axis. This implant is referred to as a size "++ML, I SI" implant.

The posterior articular surface 801 has a dome-shaped surface. A point 808 on the dome-shaped surface defines the posterior-most point of the orthopaedic implant 840. As can be seen in FIG. 18B, an imaginary line 818 extending through the posterior-most point 808 of the posterior articular surface 801 is parallel to an imaginary line 816 extending through a midpoint 806 of the medial/lateral width of the anterior surface 802 of the patella implant 840, but is spaced apart from it in the medial direction. A distance ($I_2$) is defined by measuring a length between the imaginary line 818 extending through the posterior-most point 808 and the imaginary line 816 extending through the midpoint 806 of the medial/lateral width. Imaginary lines 816 and 818 are perpendicular to flat anterior surface 802. Although FIGS. 18B and 18D illustrate the posterior-most point 808 of the posterior articular surface 801 offset in a medial direction along the mediolateral axis, it should be understood that the orthopaedic implant 840 can be configured so that the posterior-most point 808 of the posterior articular surface 801 is offset by a similar distance $I_2$ in a lateral direction along the mediolateral axis.

FIGS. 19A-19D show an embodiment of a monoblock patella orthopaedic size "++ ML, S SI" 850 of the present disclosure. The orthopaedic implant 850 features a high offset of the posterior articular surface 801 relative to the anatomical outside profile. The orthopaedic implant 850 also includes a flat anterior surface 802 having a number of fixation members, such as pegs 803, extending away therefrom. The pegs 803 are configured to be implanted into a surgically prepared posterior surface of the patient's natural patella. In such a way, the posterior articular surface 801 of the orthopaedic implant 850 faces toward the femur thereby allowing the posterior articular surface 801 to articulate with the femoral condyles during flexion and extension of the patient's knee. The posterior articular surface 801 is sufficiently designed to articulate against the natural distal femur or a prosthetic distal femur. Bone cement 805 can be applied to the cement pockets 806 in the underside of the flat anterior surface 802.

Figure 19:
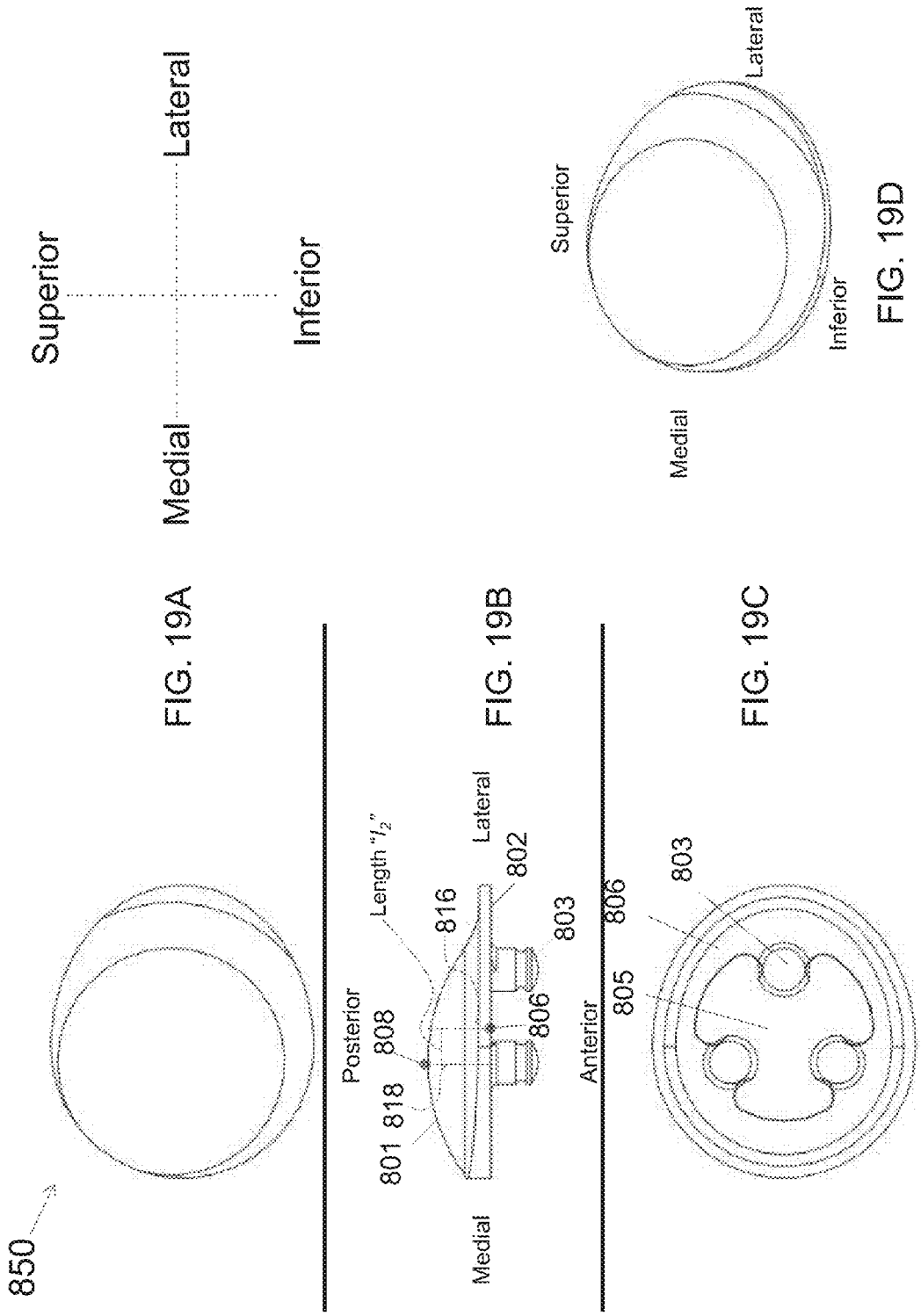
FIGS. 19A-19D show an embodiment of a monoblock patella orthopaedic implant being offset in the medial direction along the medial-lateral axis, and having a superior offset along the superior-inferior axis. This implant is referred to as a size "++ML, S SI" implant.

The posterior articular surface 801 has a dome-shaped surface. A point 808 on the dome-shaped surface defines the posterior-most point of the orthopaedic implant 850. As can be seen in FIG. 19B, an imaginary line 818 extending through the posterior-most point 808 of the posterior articular surface 801 is parallel to an imaginary line 816 extending through a midpoint 806 of the medial/lateral width of the anterior surface 802 of the patella implant 850, but is spaced apart from it in the medial direction. A distance ($I_2$) is defined by measuring a length between the imaginary line 818 extending through the posterior-most point 808 and the imaginary line 816 extending through the midpoint 806 of the medial/lateral width. imaginary lines 816 and 818 are perpendicular to flat anterior surface 802. Although FIGS. 19B and 19D illustrate the posterior-most point 808 of the posterior articular surface 801 offset in a medial direction along the mediolateral axis, it should be understood that the orthopaedic implant 850 can be configured so that the posterior-most point 808 of the posterior articular surface 801 is offset by a similar distance $I_2$ in a lateral direction along the mediolateral axis.

FIGS. 20A-20D show an embodiment of a monoblock patella orthopaedic size "0 ML, I SI" implant 860 of the present disclosure. The orthopaedic implant 860 features a high offset of the posterior articular surface 801 relative to the anatomical outside profile. The orthopaedic implant 860 also includes a flat anterior surface 802 having a number of fixation members, such as pegs 803, extending away therefrom. The pegs 803 are configured to be implanted into a surgically prepared posterior surface of the patient's natural patella. In such a way, the posterior articular surface 801 of the orthopaedic implant 860 faces toward the femur thereby allowing the posterior articular surface 801 to articulate with the femoral condyles during flexion and extension of the patient's knee. The posterior articular surface 801 is sufficiently designed to articulate against the natural distal femur or a prosthetic distal femur. Bone cement 805 can be applied to the cement pockets 806 in the underside of the flat anterior surface 802.

Figure 20:
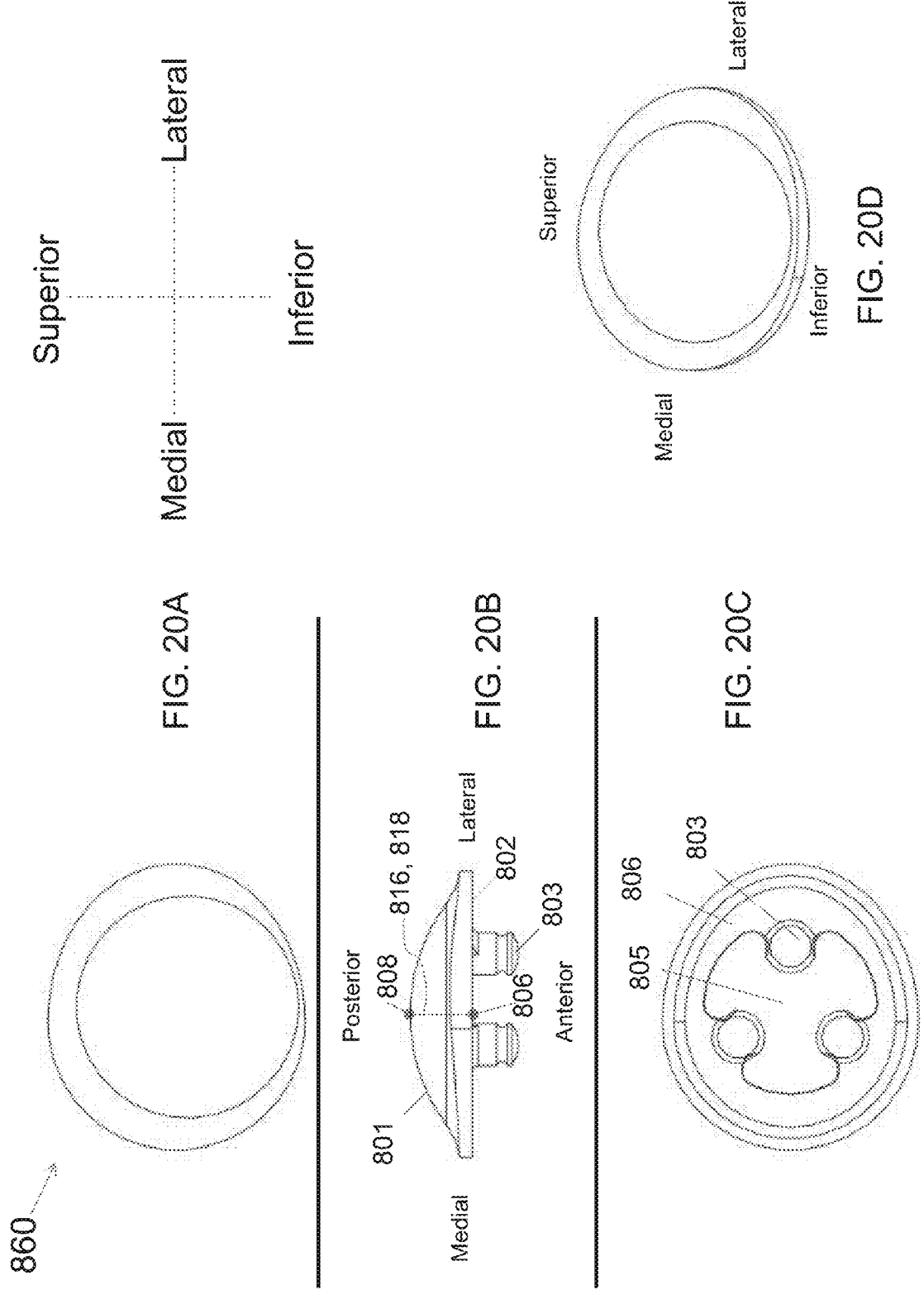
FIGS. 20A-20D show an embodiment of a monoblock patella orthopaedic implant in a neutral position along the medial-lateral axis (i.e., having no medial-lateral offset), and having an inferior offset along the superior-inferior axis. This implant is referred to as a size "0 ML, I SI" implant.

The posterior articular surface 801 has a dome-shaped surface. A point 808 on the dome-shaped surface defines the posterior-most point of the orthopaedic implant 860. As can be seen in FIG. 20B, an imaginary line 818 extending through the posterior-most point 808 of the posterior articular surface 801 overlaps an imaginary line 816 extending through a midpoint 806 of the medial/lateral width of the anterior surface 802 of the patella implant 860. Since the imaginary line 816 extending through the midpoint 806 and the imaginary line 818 extending through the posterior-most point 808 overlap one another, there is no offset of the posterior articular surface 801 along the medial-lateral axis of the flat anterior surface 802. Imaginary lines 816 and 818 are perpendicular to flat anterior surface 802.

FIGS. 21A-21D show an embodiment of a monoblock patella orthopaedic size "0 ML, 0 SI" implant 870 of the present disclosure. The orthopaedic implant 870 features a high offset of the posterior articular surface 801 relative to the anatomical outside profile. The orthopaedic implant 870 also includes a flat anterior surface 802 having a number of fixation members, such as pegs 803, extending away therefrom. The pegs 803 are configured to be implanted into a surgically prepared posterior surface of the patient's natural patella. In such a way, the posterior articular surface 801 of the orthopaedic implant 870 faces toward the femur thereby allowing the posterior articular surface 801 to articulate with the femoral condyles during flexion and extension of the patient's knee. The posterior articular surface 801 is sufficiently designed to articulate against the natural distal femur or a prosthetic distal femur. Bone cement 805 can be applied to the cement pockets 806 in the underside of the flat anterior surface 802.

Figure 21:
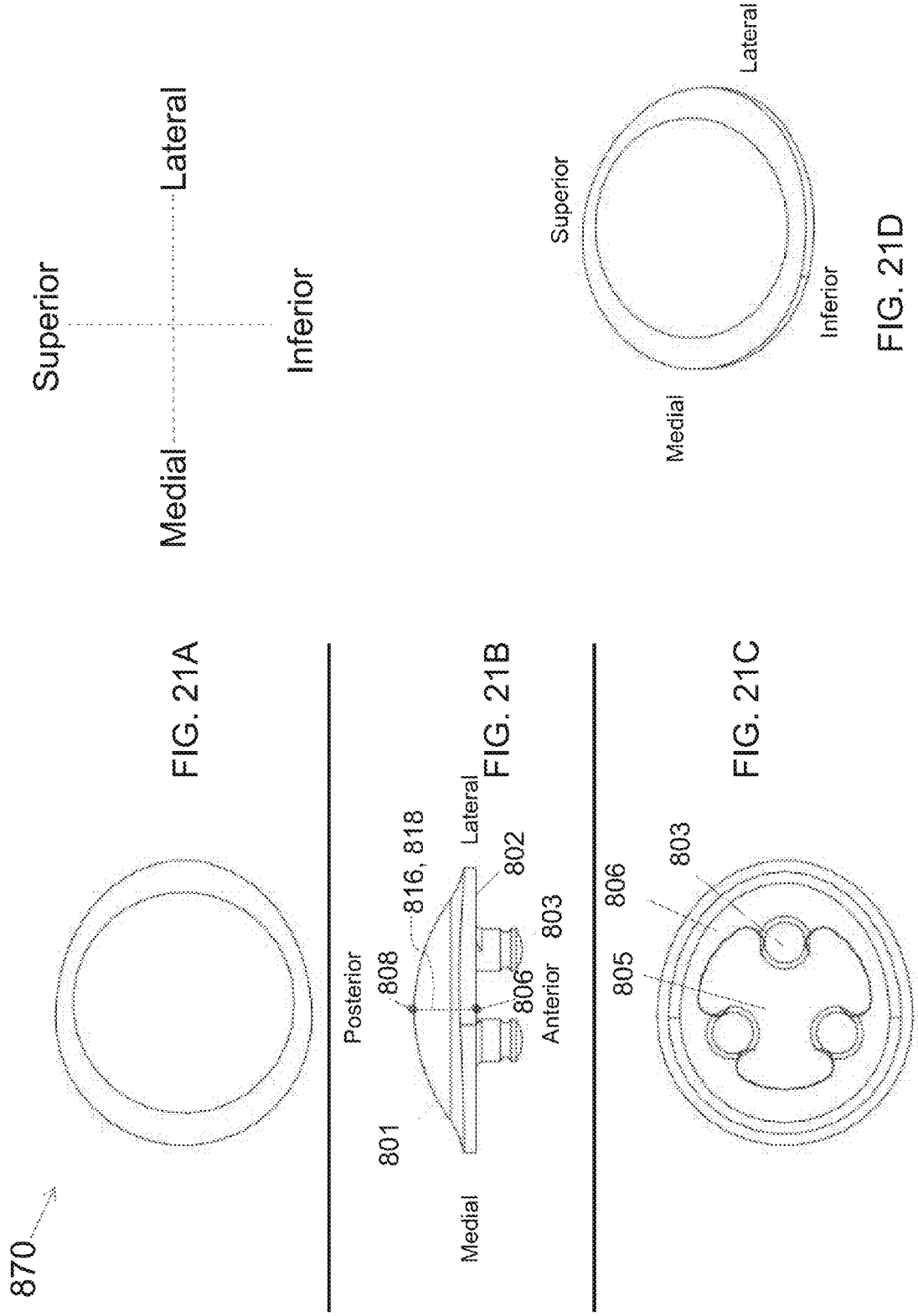
FIGS. 21A-21D show an embodiment of a monoblock patella orthopaedic implant in a neutral position along the medial-lateral axis (i.e., having no medial-lateral offset), and in a neutral position along the superior-inferior axis. This implant is referred to as a size "0 ML, 0 SI" implant.

The posterior articular surface 801 has a dome-shaped surface. A point 808 on the dome-shaped surface defines the posterior-most point of the orthopaedic implant 870. As can be seen in FIG. 21B, an imaginary line 818 extending through the posterior-most point 808 of the posterior articular surface 801 overlaps an imaginary line 816 extending through a midpoint 806 of the medial/lateral width of the anterior surface 802 of the patella implant 870. Since the imaginary line 816 extending through the midpoint 806 and the imaginary line 818 extending through the posterior-most point 808 overlap one another, there is no offset of the posterior articular surface 801 along the medial-lateral axis of the flat anterior surface 802. Imaginary lines 816 and 818 are perpendicular to flat anterior surface 802.

FIGS. 22A-22D show an embodiment of a monoblock patella orthopaedic size "0 ML, S SI" implant 880 of the present disclosure. The orthopaedic implant 880 features a high offset of the posterior articular surface 801 relative to the anatomical outside profile. The orthopaedic implant 880 also includes a flat anterior surface 802 having a number of fixation members, such as pegs 803, extending away therefrom. The pegs 803 are configured to be implanted into a surgically prepared posterior surface of the patient's natural patella. In such a way, the posterior articular surface 801 of the orthopaedic implant 880 faces toward the femur thereby allowing the posterior articular surface 801 to articulate with the femoral condyles during flexion and extension of the patient's knee. The posterior articular surface 801 is sufficiently designed to articulate against the natural distal femur or a prosthetic distal femur. Bone cement 805 can be applied to the cement pockets 806 in the underside of the flat anterior surface 802.

Figure 22:
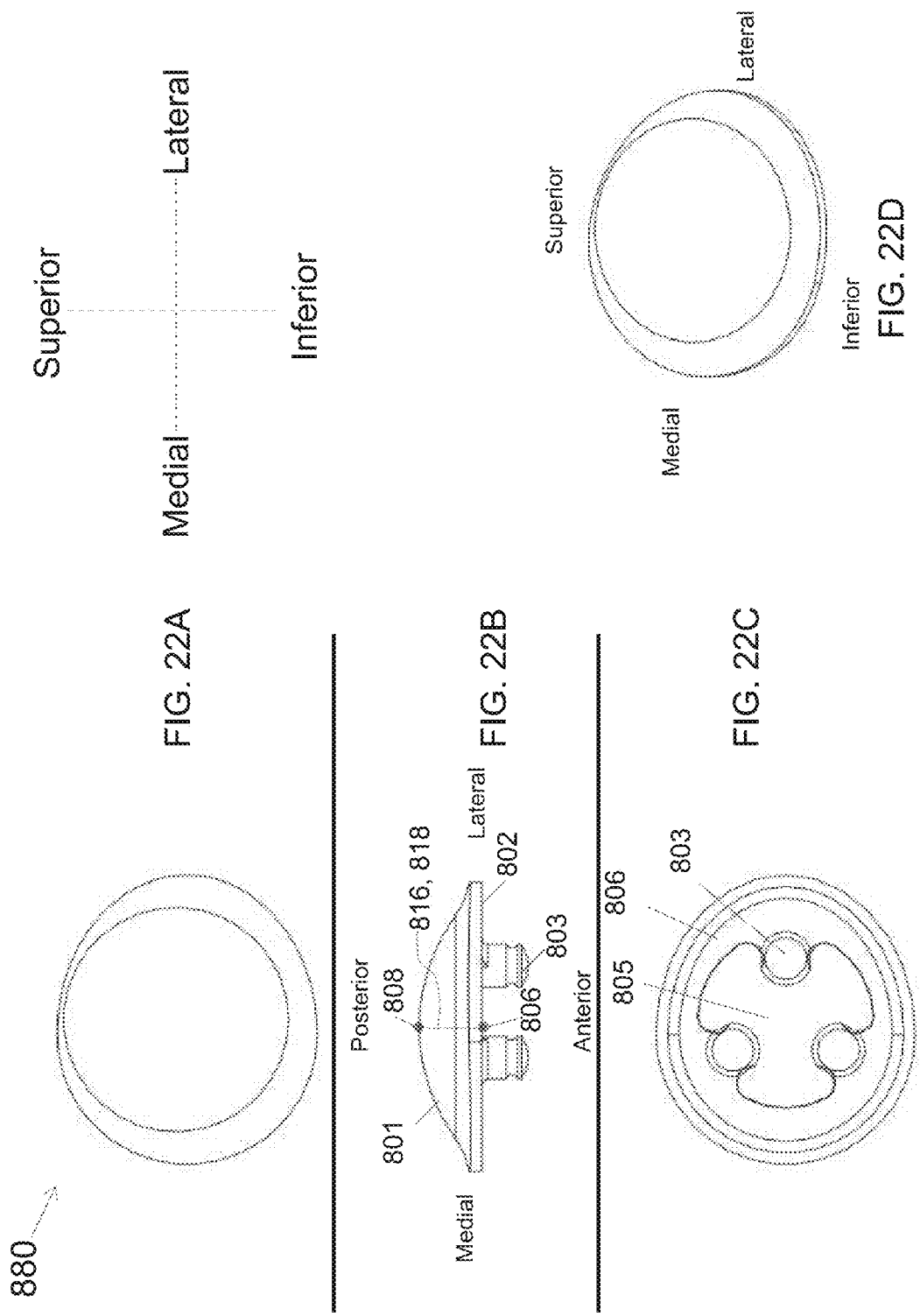
FIGS. 22A-22D show an embodiment of a monoblock patella orthopaedic implant in a neutral position along the medial-lateral axis (i.e., having no medial-lateral offset), and having a superior offset along the superior-inferior axis. This implant is referred to as a size "0 MI, S SI" implant.

The posterior articular surface 801 has a dome-shaped surface. A point 808 on the dome-shaped surface defines the posterior-most point of the orthopaedic implant 880. As can be seen in FIG. 22B, an imaginary line 818 extending through the posterior-most point 808 of the posterior articular surface 801 overlaps an imaginary line 816 extending through a midpoint 806 of the medial/lateral width of the anterior surface 802 of the patella implant 880. Since the imaginary line 816 extending through the midpoint 806 and the imaginary line 818 extending through the posterior-most point 808 overlap one another, there is no offset of the posterior articular surface 801 along the medial-lateral axis of the flat anterior surface 802. Imaginary lines 816 and 818 are perpendicular to flat anterior surface 802.

A surgeon selects the appropriate monoblock patella orthopaedic implant (800, 810, 820, 830, 840, 850, 860, 870 and 880, for example) from the second patella orthopaedic implant kit, which is defined by the size of the anatomical outside profile (first parameter), the mediolateral offset of the dome-shaped articular surface relative to the anatomical outside profile (second parameter), and the superoinferior offset of the dome-shaped articular surface relative to the anatomical outside profile (third parameter) in order to duplicate the geometry of the trial patella. Table II lists different patella orthopaedic implants of the present invention assuming 6 anatomical sizes available under 3 ML offset options, and 3 SI offset options resulting in 54 monoblock patella orthopaedic implants (i.e., 6×3×3). More generally, a kit available under (m) sizes, each available under (n) ML offset options and (p) SI offset options will result in (m*n*p) monoblock patella orthopaedic implants

TABLE II

| Size | A | | | B | | |
|---|---|---|---|---|---|---|
| ML Offset | 0 | + | ++ | 0 | + | ++ |
| SI Offset | S O I | S O I | S O I | S O I | S O I | S O I |
| Size | C | | | D | | |
| ML Offset | 0 | + | ++ | 0 | + | ++ |
| SI Offset | S O I | S O I | S O I | S O I | S O I | S O I |
| Size | E | | | F | | |
| ML Offset | 0 | + | ++ | 0 | + | ++ |
| SI Offset | S O I | S O I | S O I | S O I | S O I | S O I |

Figure 23:
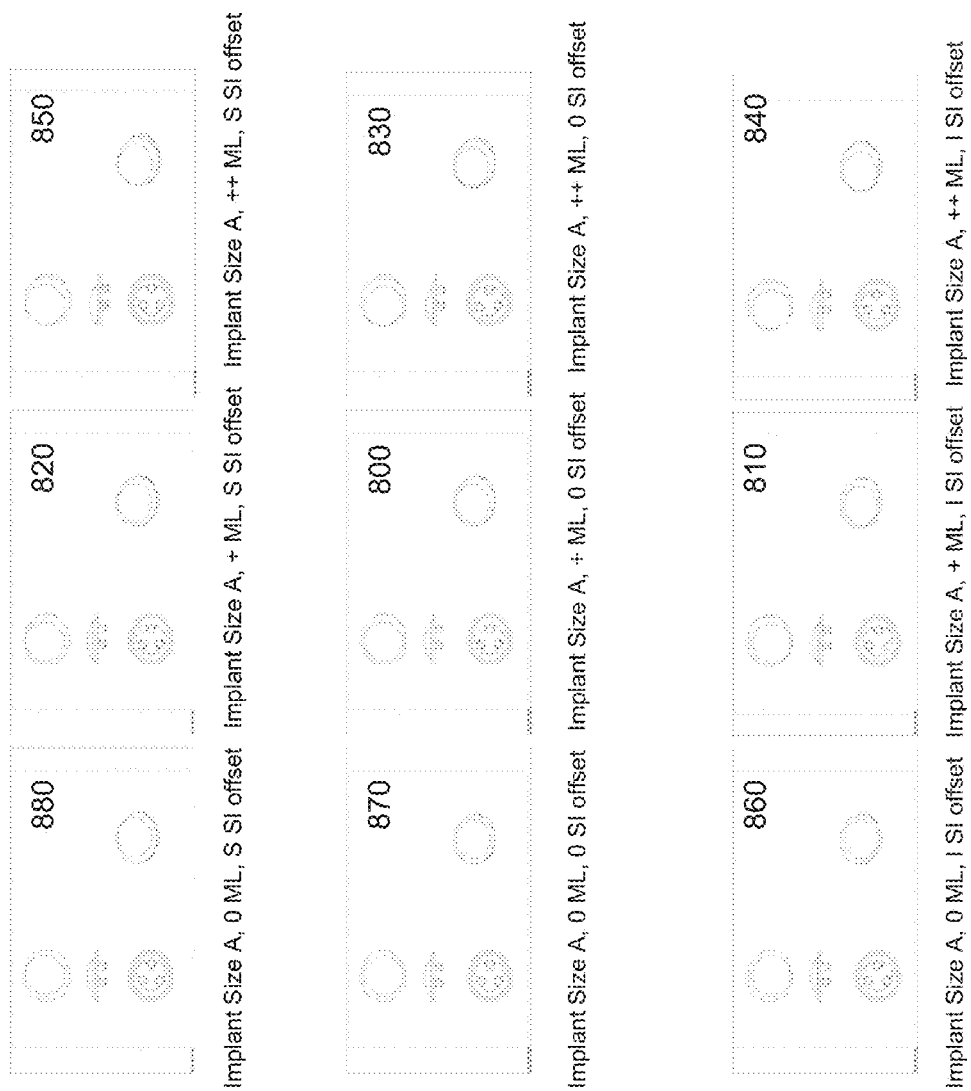
FIG. 23 shows a set of monoblock patella orthopaedic implants of the present invention, where the anatomical baseplates are all the same size (for example 35 mm) and where there is at least one of a medial-lateral offset or a superior-inferior offset.

FIG. 23 shows a set of monoblock patella orthopaedic implants of the present invention, where the anatomical baseplates are all the same size (for example 35 mm, size "A"), and where there is at least one of a medial-lateral offset or a superior-inferior offset of the dome-shaped articular surface. The nine (9) monoblock patella orthopaedic implants are: (880) "0 ML, S SI", (820) "+ ML, S SI", (850) "++ ML, S SI", (870) "0 ML, 0 SI", (800) "+ ML, 0 SI", (830) "++ ML, 0 SI", (860) "0 ML, I SI", (810) "+ ML, I SI" and (840) "++ ML, I SI".

It will be appreciated that several of the above-disclosed and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

What is claimed is:

1. A patella trial comprising:
   a baseplate having a medial-lateral axis and a superior-inferior axis, and an opening; and
   a mobile articular surface member in direct physical contact with the baseplate, having a shaft configured to be inserted into the opening in the baseplate,
   wherein the baseplate has an anterior surface configured to temporarily attach to a posterior surface of a resected patella,
   wherein the baseplate has a non-circular shape to cover the posterior surface of the resected patella,
   wherein the baseplate has a posterior surface having at least one marking defining at least one of a medial-lateral offset or a superior-inferior offset of the articular surface member,
   wherein the mobile articular surface member is configured to allow adjustment of the articulation of the resected patella and a femur, independently of the coverage of the posterior surface of the resected patella, and
   wherein the shaft of the mobile articular member and the opening in the baseplate are configured to (i) attach the mobile articular member to the baseplate, and allow the selective movement of the mobile articular member along at least one of the medial-lateral axis or the superior-inferior axis of the baseplate.

2. The patella trial of claim 1 wherein the anterior surface of the baseplate is substantially flat and includes at least one peg extending outwardly from the anterior surface configured to temporarily attach to the posterior surface of the resected patella.

3. The patella trial of claim 1 wherein the mobile articular surface member is dome-shaped.

4. The patella trial of claim 1 wherein the mobile articular surface member is smaller in size than the baseplate.

5. A system comprising:
   a patella trial comprising:
   a baseplate having a medial-lateral axis and a superior-inferior axis, and an opening; and
   a mobile articular surface member in direct physical contact with the baseplate, having a shaft configured to be inserted into the opening of the baseplate,
   wherein the baseplate has an anterior surface configured to temporarily attach to a posterior surface of a resected patella,
   wherein the baseplate has a non-circular shape to cover the posterior surface of the resected patella,
   wherein the baseplate has a posterior surface having at least one marking defining at least one of a medial-lateral offset or a superior-inferior offset of the articular surface member relative to the baseplate,
   wherein the mobile articular surface member is configured to allow adjustment of the articulation of the resected patella and a femur, independently of the coverage of the posterior surface of the resected patella, and
   wherein the shaft of the mobile articular member and the opening in the baseplate are configured to (i)

attach the mobile articular member to the baseplate, and allow the selective movement of the mobile articular member along at least one of the medial-lateral axis or the superior-inferior axis of the baseplate; and an orthopaedic implant comprising:
a one piece patella component having a posterior articular surface and a flat anterior surface having at least one fixation member extending outwardly therefrom,
wherein the anterior surface has a medial/lateral width with a midpoint,
wherein the posterior articular surface has a posterior-most point,
wherein an imaginary line extending through the posterior-most point of the posterior articular surface is parallel to an imaginary line extending through the midpoint of the medial/lateral width of the anterior surface, and
wherein a distance (I) is defined by measuring a length between the imaginary line extending through the posterior-most point and the imaginary line extending through the midpoint of the medial/lateral width;
wherein the orthopaedic implant is selected from a set of orthopaedic implants,
wherein each orthopaedic implant in the set having a different I, and
wherein the chosen orthopaedic implant is selected based on the offset of the articular surface member relative to the baseplate on the patella trial, and the coverage of the posterior surface of the resected patella.

6. The system of claim 5 wherein the anterior surface of the patella trial baseplate is substantially flat and includes at least one peg extending outwardly from the anterior surface configured to temporarily attach to the posterior surface of the resected patella.

7. The system of claim 5 wherein the mobile articular surface member of the patella trial is dome-shaped.

8. The system of claim 5 wherein the baseplate of the patella trial is made from a solid piece material having a non-circular shape.

9. The system of claim 5 wherein each orthopaedic implant is embodied as a monolithic polymer body.

10. The system of claim 5 wherein each orthopaedic implant is formed from an ultra-high molecular weight polyethylene.

11. The system of claim 5 wherein each orthopaedic implant is formed from a ceramic material.

12. The system of claim 5 wherein each orthopaedic implant is formed from a metal material.

13. A kit comprising:
a patella trial comprising:
a baseplate having a medial-lateral axis and a superior-inferior axis, and an opening; and
a mobile articular surface member in direct physical contact with the baseplate, having a shaft configured to be inserted into the opening in the baseplate,
wherein the baseplate has an anterior surface configured to temporarily attach to a posterior surface of a resected patella,
wherein the baseplate has a non-circular shape to cover the posterior surface of the resected patella,
wherein the baseplate has a posterior surface having at least one marking defining at least one of a medial-lateral offset or a superior-inferior offset of the articular surface member,
wherein the mobile articular surface member is configured to allow adjustment of the articulation of the resected patella and a femur,
independently of the coverage of the posterior surface of the resected patella, and
wherein the shaft of the mobile articular member and the opening in the baseplate are configured to (i) attach the mobile articular member to the baseplate, and allow the selective movement of the mobile articular member along at least one of the medial-lateral axis or the superior-inferior axis of the baseplate;

a first orthopaedic implant comprising:
a one piece patella component having a posterior articular surface and a flat anterior surface having at least one fixation member extending outwardly therefrom,
wherein the anterior surface has a medial/lateral width with a midpoint,
wherein the posterior articular surface has a posterior-most point,
wherein an imaginary line extending through the posterior-most point of the posterior articular surface is parallel to an imaginary line extending through the midpoint of the medial/lateral width of the anterior surface, and
wherein a first distance ($I_1$) is defined by measuring a length between the imaginary line extending through the posterior-most point and the imaginary line extending through the midpoint of the medial/lateral width; and a second orthopaedic implant comprising:
a one piece patella component having a posterior articular surface and a flat anterior surface having at least one fixation member extending outwardly therefrom,
wherein the anterior surface has a medial/lateral width with a midpoint,
wherein the posterior articular surface has a posterior-most point,
wherein an imaginary line extending through the posterior-most point of the posterior articular surface is parallel to an imaginary line extending through the midpoint of the medial/lateral width of the anterior surface, and
wherein a second distance ($I_2$) is defined by measuring a length between the imaginary line extending through the posterior-most point and the imaginary line extending through the midpoint of the medial/lateral width; and
wherein $I_1$ of the first orthopaedic implant is not equivalent to $I_2$ of the second orthopaedic implant.

14. The kit of claim 13 wherein the anterior surface of the patella trial baseplate is substantially flat and includes at least one peg extending outwardly from the anterior surface configured to temporarily attach to the posterior surface of the resected patella.

15. The kit of claim 13 wherein the baseplate of the patella trial is made from a solid piece material having a non-circular shape.

16. The kit of claim 13 wherein the first orthopaedic implant and the second orthopaedic implant are embodied as a monolithic polymer body.

17. The kit of claim 13 wherein the first orthopaedic implant and the second orthopaedic implant are formed from an ultra-high molecular weight polyethylene.

18. The kit of claim 13 wherein the first orthopaedic implant and the second orthopaedic implant are formed from a ceramic material.

19. The kit of claim 13 wherein the first orthopaedic implant and the second orthopaedic implant are formed from a metal material.

* * * * *